(12) United States Patent
Heruth et al.

(10) Patent No.: US 7,491,181 B2
(45) Date of Patent: Feb. 17, 2009

(54) COLLECTING ACTIVITY AND SLEEP QUALITY INFORMATION VIA A MEDICAL DEVICE

(75) Inventors: Kenneth T. Heruth, Edina, MN (US); Keith A. Miesel, St. Paul, MN (US)

(73) Assignee: Medtronic, Inc., Minneapolis, MN (US)

(*) Notice: Subject to any disclaimer, the term of this patent is extended or adjusted under 35 U.S.C. 154(b) by 158 days.

(21) Appl. No.: 10/825,955

(22) Filed: Apr. 15, 2004

(65) Prior Publication Data

US 2005/0209511 A1    Sep. 22, 2005

Related U.S. Application Data

(60) Provisional application No. 60/553,785, filed on Mar. 16, 2004.

(51) Int. Cl.
*A61B 5/103* (2006.01)
*A61B 5/117* (2006.01)
*A61N 1/00* (2006.01)

(52) U.S. Cl. .................. 600/595; 600/587; 600/594; 607/19

(58) Field of Classification Search ............. 600/595, 600/594, 587; 607/19
See application file for complete search history.

(56) References Cited

U.S. PATENT DOCUMENTS

| | | | |
|---|---|---|---|
| 4,297,685 A | 10/1981 | Brainard, II | |
| 4,543,955 A | 10/1985 | Schroeppel | |
| 4,550,736 A | 11/1985 | Broughton et al. | |
| 4,771,780 A | 9/1988 | Sholder | |
| 4,776,345 A | 10/1988 | Cohen et al. | |
| 4,846,195 A | 7/1989 | Alt | |
| 5,040,536 A | 8/1991 | Riff | |
| 5,058,584 A | 10/1991 | Bourgeois | |
| 5,125,412 A | 6/1992 | Thornton | |

(Continued)

FOREIGN PATENT DOCUMENTS

DE    198 31 109    1/2000

(Continued)

OTHER PUBLICATIONS

M.T. Smith et al, "Presleep Cognitions in Patients with Insomnia Secondary to Chronic Pain", Journal of Behavioral Medicine, vol. 24, No. 1, 2001.

(Continued)

*Primary Examiner*—Max Hindenburg
*Assistant Examiner*—Jeffrey G Hoekstra
(74) *Attorney, Agent, or Firm*—Shumaker & Sieffert, P.A.

(57) ABSTRACT

A device, such as an implantable medical device (IMD) or a programming device, determines when a patient is attempting to sleep. When the device determines that the patient is attempting to sleep, the device determines values for one or more metrics that indicate the quality of a patient's sleep based on at least one physiological parameter of the patient. When the device determines that the patient is not attempting to sleep, the device periodically determines activity levels of the patient. Activity metric values may be determined based on the determined activity levels. A clinician may use sleep quality information and patient activity information presented by a programming device to, for example, evaluate the effectiveness of therapy delivered to the patient by the medical device.

28 Claims, 10 Drawing Sheets

U.S. PATENT DOCUMENTS

| | | |
|---|---|---|
| 5,154,180 A | 10/1992 | Blanchet et al. |
| 5,233,984 A | 8/1993 | Thompson |
| 5,275,159 A | 1/1994 | Griebel |
| 5,335,657 A | 8/1994 | Terry, Jr. et al. |
| 5,337,758 A | 8/1994 | Moore et al. |
| 5,342,409 A | 8/1994 | Mullett |
| 5,469,861 A | 11/1995 | Piscopo et al. |
| 5,476,483 A | 12/1995 | Bornzin et al. |
| 5,514,162 A | 5/1996 | Bornzin et al. |
| 5,593,431 A | 1/1997 | Sheldon |
| 5,622,428 A | 4/1997 | Bonnet |
| 5,645,053 A | 7/1997 | Remmers et al. |
| 5,732,696 A | 3/1998 | Rapoport et al. |
| 5,782,884 A | 7/1998 | Stotts et al. |
| 5,832,932 A | 11/1998 | Elsberry et al. |
| 5,895,371 A | 4/1999 | Levitas et al. |
| 5,904,708 A | 5/1999 | Goedeke |
| 5,904,780 A | 5/1999 | Tomoyasu |
| 5,919,149 A | 7/1999 | Allum |
| 5,941,906 A | 8/1999 | Barreras, Sr. et al. |
| 5,944,680 A | 8/1999 | Christopherson et al. |
| 5,999,846 A | 12/1999 | Pardey et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,102,874 A | 8/2000 | Stone et al. |
| 6,120,467 A | 9/2000 | Schallhorn |
| 6,128,534 A | 10/2000 | Park et al. |
| 6,157,857 A | 12/2000 | Dimpfel |
| 6,165,143 A | 12/2000 | van Lummel |
| 6,259,948 B1 | 7/2001 | Florio et al. |
| 6,273,856 B1 | 8/2001 | Sun et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,351,672 B1 * | 2/2002 | Park et al. .................. 607/19 |
| 6,366,813 B1 | 4/2002 | DiLorenzo |
| 6,416,471 B1 | 7/2002 | Kumar et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,514,218 B2 | 2/2003 | Yamamoto |
| 6,539,249 B1 | 3/2003 | Kadhiresan et al. |
| 6,574,507 B1 | 6/2003 | Bonnet |
| 6,605,038 B1 | 8/2003 | Teller et al. |
| 6,611,783 B2 | 8/2003 | Kelly, Jr. et al. |
| 6,659,968 B1 | 12/2003 | McClure |
| 6,687,538 B1 | 2/2004 | Hrdlicka et al. |
| 6,731,984 B2 | 5/2004 | Chu et al. |
| 6,752,766 B2 | 6/2004 | Kowallik et al. |
| 6,773,404 B2 | 8/2004 | Poezevera et al. |
| 6,819,956 B2 | 11/2004 | DiLorenzo |
| 6,878,121 B2 | 4/2005 | Krausman et al. |
| 6,881,192 B1 | 4/2005 | Park |
| 6,884,596 B2 | 4/2005 | Civelli et al. |
| 6,890,306 B2 | 5/2005 | Poezevera |
| 6,928,324 B2 | 8/2005 | Park et al. |
| 6,964,641 B2 * | 11/2005 | Cho et al. .................. 600/529 |
| 7,162,304 B1 | 1/2007 | Bradley |
| 7,209,787 B2 | 4/2007 | DiLorenzo |
| 2001/0031930 A1 | 10/2001 | Roizen et al. |
| 2001/0037067 A1 | 11/2001 | Tchou et al. |
| 2002/0077562 A1 | 6/2002 | Kalgren et al. |
| 2002/0091308 A1 | 7/2002 | Kipshidze et al. |
| 2002/0161412 A1 | 10/2002 | Sun et al. |
| 2002/0169485 A1 | 11/2002 | Pless et al. |
| 2002/0177882 A1 | 11/2002 | DiLorenzo |
| 2002/0193697 A1 | 12/2002 | Cho et al. |
| 2002/0193839 A1 | 12/2002 | Cho et al. |
| 2003/0004423 A1 | 1/2003 | Lavie et al. |
| 2003/0139692 A1 | 7/2003 | Barrey et al. |
| 2003/0149457 A1 | 8/2003 | Tcheng et al. |
| 2003/0153953 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171791 A1 | 9/2003 | KenKnight et al. |
| 2003/0195588 A1 | 10/2003 | Fischell et al. |
| 2003/0212445 A1 | 11/2003 | Weinberg |
| 2004/0002741 A1 | 1/2004 | Weinberg |
| 2004/0002742 A1 | 1/2004 | Florio |
| 2004/0015103 A1 | 1/2004 | Aminian et al. |
| 2004/0049132 A1 | 3/2004 | Barron et al. |
| 2004/0102814 A1 | 5/2004 | Sorensen et al. |
| 2004/0111040 A1 | 6/2004 | Ni et al. |
| 2004/0111041 A1 * | 6/2004 | Ni et al. .................. 600/544 |
| 2005/0021103 A1 | 1/2005 | DiLorenzo |
| 2005/0021104 A1 | 1/2005 | DiLorenzo |
| 2005/0039745 A1 | 2/2005 | Stahmann et al. |
| 2005/0042589 A1 | 2/2005 | Hatlestad et al. |
| 2005/0061320 A1 | 3/2005 | Lee et al. |
| 2005/0065560 A1 | 3/2005 | Lee et al. |
| 2005/0076908 A1 | 4/2005 | Lee et al. |
| 2005/0085738 A1 | 4/2005 | Stahmann et al. |
| 2005/0113710 A1 | 5/2005 | Stahmann et al. |
| 2005/0119703 A1 | 6/2005 | DiLorenzo |
| 2005/0143617 A1 | 6/2005 | Auphan |
| 2005/0177192 A1 | 8/2005 | Rezai et al. |
| 2005/0215847 A1 | 9/2005 | Heruth et al. |
| 2005/0222626 A1 | 10/2005 | DiLorenzo |
| 2005/0240086 A1 | 10/2005 | Akay |
| 2005/0240242 A1 | 10/2005 | DiLorenzo |
| 2005/0245790 A1 | 11/2005 | Bergfalk et al. |
| 2006/0224191 A1 | 10/2006 | DiLorenzo |
| 2006/0293720 A1 | 12/2006 | DiLorenzo |
| 2007/0073355 A1 | 3/2007 | DiLorenzo |
| 2007/0142862 A1 | 6/2007 | DiLorenzo |

FOREIGN PATENT DOCUMENTS

| | | |
|---|---|---|
| DE | 100 24 103 | 11/2001 |
| EP | 0 564 803 A1 | 10/1993 |
| EP | 0 849 715 B1 | 6/1998 |
| EP | 1 195 139 A1 | 4/2002 |
| EP | 1 291 036 A2 | 3/2003 |
| EP | 1 308 182 A2 | 5/2003 |
| EP | 1 437 159 A1 | 7/2004 |
| EP | 1 322 227 B1 | 12/2005 |
| GB | 2 330 912 | 5/1999 |
| WO | WO 98/00197 | 1/1998 |
| WO | WO 99/13765 | 3/1999 |
| WO | WO 01/37930 | 5/2001 |
| WO | WO 02/28282 | 4/2002 |
| WO | WO 02/28282 A1 | 4/2002 |
| WO | WO 02/28285 | 4/2002 |
| WO | WO 02/41771 A1 | 5/2002 |
| WO | WO 02/087433 | 11/2002 |
| WO | WO 02/096512 A1 | 12/2002 |
| WO | WO 02/100267 | 12/2002 |
| WO | WO 02/100267 A1 | 12/2002 |
| WO | WO 03/024325 | 3/2003 |
| WO | WO 03/051356 | 6/2003 |
| WO | WO 03/051356 A1 | 6/2003 |
| WO | WO 03/065891 A2 | 8/2003 |
| WO | WO 05/028029 | 3/2005 |
| WO | WO 05-035050 | 4/2005 |
| WO | WO 2005/035050 | 4/2005 |

OTHER PUBLICATIONS

Suanne Goodrich et al., "The Predictions of Pain Using Measures of Sleep Quality", Pain Digest (1998) 8:23-25.

"Analysis of heart rate dynamics by methods derived from nonlinear mathematics: Clinical applicability and prognostic significance" http:/herkules.oulu.fi.isbn9514250133/html/x222.html (2004).

U.S. Patent Application entitled "Detecting Sleep", U.S. Appl. No. 10/825,964, filed on Apr. 15, 2004.

U.S. Patent Application entitled "Collecting Posture Information to Evaluate Therapy", U.S. Appl. No. 10/826,926, filed Apr. 15, 2004.

U.S. Patent Application entitled "Collecting Activity Information to Evaluate Therapy", U.S. Appl. No. 10/825,965, filed Apr. 15, 2004.

U.S. Patent Application entitled "Collecting Sleep Quality Information via a Medical Device", U.S. Appl. No. 10/826,925, filed Apr. 15, 2004.

U.S. Patent Application entitled "Controlling Therapy Based on Sleep Quality", U.S. Appl. No. 10/825,953, filed Apr. 15, 2004.

U.S. Patent Application entitled "Sensitivity Analysis for Selecting Therapy Parameter Sets", U.S. Appl. No. 11/081,873, filed Mar. 16, 2005.

International Search Report and Written Opinion for corresponding PCT Application Serial No. PCT/US2005/008789, mailed Jul. 6, 2005 (14 pages).

"Watch," Wikipedia, the free encyclopedia, 6 pgs., http://en.wikipedia.org/wiki/Watch, (2006).

"IBM & Citizen Watch develop Linux-based 'WatchPad'," 5 pgs., http://www.linuxdevices.com/news/NS6580187845.html, (2006).

Tuisku, Katinka, "Motor Activity Measured By Actometry in Neuropsychiatric Disorders," Department of Psychiatry, University of Helsinki, Helsinki, Finland, 115 pgs., (2002).

Kassam, M., "2005 EDP Topic 'MK4': Tremor Data-Logger for Parkinson's Disease Patients," http://www.ee.ryerson.ca/~courses/edp2005/MK4.html, 3 pgs., (2006).

"Design Competition: Runners-Up for the Best Three Designs," EPN, vol. 26, No. 1, (2002).

"MiniMitter® Physiological and Behavioral Monitoring for Humans an Animals," http://www.minimitter.com/Products/Actiwatch, 3 pgs., (2006).

Notification of Transmittal of the International Preliminary Report on Patentability for corresponding PCT Application Serial No. PCT/US2005/008789, dated Mar. 16, 2006, 12 pgs Amzica, "Physiology of Sleep and Wakefulness as it Relates to the Physiology of Epilepsy," Journal of Clinical Neurophysiology, American Clinical Neurophysiology Society, 19(6), pp. 488-503, (2002).

Dinner, "Effect of Sleep of Epilepsy," Journal of Clinical Neurophysiology, American Clinical Neurophysiology Society, 19(6), pp. 504-513, (2002).

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, (2002).

Mendez et al. "Interactions Between Sleep and Epilepsy," Journal of Clinical Neurophysiology, American Clinical Neurophysiology Society, 18(2), pp. 106-127, (2001).

Kerr et al., "Analysis of the sit-stand-sit movement cycle in normal subjects," Clinical Biomechanics, vol. 12, No. 4, pp. 236-245, (1997).

Aminian et al. "Physical Activity Monitoring Based on Accelerometry: Validation and Comparison with Video Observation," Medical & Biological Engineering & Computing, vol. 37, No. 2, pp. 304-308 (1999).

Medcare—A Global Leader in Sleep Diagnostics, Embletta Recording System, http://www.medcare.com/products/diagnostic/embletta/, 2 pgs. Jan. 31, 2005.

Medcare—A Global Leader in Sleep Diagnostics, Somnologica for Embletta, http://www.medcare.com/products/diagnostic/embletta/SomnoEmbletta/index.asp, 1 pg. Jan. 31, 2005.

MAP Medizin-Technologie GmbH, Poly-MESAM®, http://195.244.124.130/map/de/eng/map_med.nsf/cmsall/70564A3FCBE4188AC1256EF4.., 4 pgs. Jan. 31, 2005.

Merlin, http://www.aha.ru/~pir/english/merlin, 4 pgs. Jan. 31, 2005.

Sleep Solutions—PR Newswire: Sleep Solutions Introduces NovaSom™ QSG™ for PSG . . . , http://www.sleep-solutions.com/press_room/novasom.htm, 2 pgs. Jan. 31, 2005.

Itamar Medical Information, http://itamar-medical.com/content.asp?id=31, 2 pgs. Jan. 31, 2005.

Criticare System Inc.,-504DX Portable Pulse Oximeter, http://www.csiusa.com/504dx.html, 4 pgs. Jan. 31, 2005.

Snap® Laboratories, Product Fact Sheet, http://www.snaplab.com/mp_fact.htm, 2 pgs. Jan. 31, 2005.

Sleep Strip & Bite Strip, http://www.quietsleep.com/snoringapnea/sleepstrip.htm, 8 pgs. Jan. 31, 2005.

"Bitestrip Flier," downloaded from Internet Archive of www.quietsleep.com dated Jan. 29, 2005 http://web.archive.org/web/20041124080003/www.quietsleep.com/pdf/Bitestrip+Flier.pdf.

"Bilateral Comparisons of the BiteStrip Bruxism Device and Masseter EMG Bruxism Events" downloaded from Internet Archive of www.quietsleep.com dated Jan. 29, 2005 http://web.archive.org/web/20041124075114/www.quietsleep.com/pdf/Bilateral+Comparisons.pdf.

"The BiteStrip: A Novel Screener for Sleep Bruxism," downloaded from Internet Archive of www.quietsleep.com dated Jan. 29, 2005 http://web.archive.org/web/20041124072922/www.quietsleep.com/pdf/BiteStrip-+Novel+Screener.pdf.

Office Action dated Jul. 5, 2006 for U.S. Appl. No. 10/825,953, filed Apr. 15, 2004, (11 pgs.).

Responsive Amendment dated Oct. 5, 2006 for U.S. Appl. No. 10/825,953, filed Apr. 15, 2004 (17 pgs.).

Office Action dated Dec. 28, 2006 for U.S. Appl. No. 10/825,953, filed Apr. 15, 2004, (9 pgs.).

Response dated Feb. 28, 2007 for U.S. Appl. No. 10/825,953, filed Apr. 15, 2004 (7 pgs.).

Office Action dated Apr. 3, 2007 for U.S. Appl. No. 10/825,953, filed Apr. 15, 2004, (8 pgs.).

Responsive Amendment dated Jun. 28, 2007 for U.S. Appl. No. 10/825,953, filed Apr. 15, 2004 (19 pgs.).

Office Action dated Jul. 3, 2007 for U.S. Appl. No. 10/826,925, filed Apr. 15, 2004, (22 pgs.).

Michael T. Smith et al., "How do sleep disturbance and chronic pain inter-relate? Insights from the longitudinal and cognitive-behavioral clinical trials literature", Sleep Medicines Reviews, (2004) 8, pp. 119-132.

Office Action dated Oct. 16, 2007 for U.S. Appl. No. 10/826,925 (29 pgs.).

Response to Office Action dated Jan. 16, 2008 for U.S. Appl. No. 10/826,925 (20 pgs.).

Office Action dated May 5, 2008 for U.S. Appl. No. 10/826,925 (12 pgs.).

Response dated Aug. 22, 2008 for U.S. Appl. No. 10/826,925 (7 pgs.).

Office Action dated May 30, 2008 for U.S. Appl. No. 11/081,811 (13 pgs.).

Responsive Amendment dated Aug. 29, 2008 for U.S. Appl. No. 11/081,811 (13 pgs.).

Office Action dated Apr. 23, 2008 for U.S. Appl. No. 11/796,811 (6 pgs.).

Responsive Amendment dated Aug. 22, 2008 for U.S. Appl. No. 11/796,811 (13 pgs.).

Office Action dated May 9, 2008 for U.S. Appl. No. 11/081,857 (10 pgs.).

Responsive Amendment dated Aug. 7, 2008 for U.S. Appl. No. 11/081,857 (13 pgs.).

Office Action dated Apr. 4, 2008 for U.S. Appl. No. 11/081,155 (9 pgs.).

van Dam et al., "Measuring physical activity in patients after surgery for a malignant tumour in the leg," The Journal of Bone & Joint Surgery, vol. 83-B, No. 7, pp. 1015-1019 (Sep. 2001).

Responsive Amendment dated Aug. 4, 2008 for U.S. Appl. No. 11/081,155 (12 pgs.).

Kassam, M., "2005 EDP Topic 'MK4': Tremor Data-Logger for Parkinson's Disease Patients," http://www.ee.ryerson,ca/~courses/edp2005/MK4.html, 3 pgs., (2006).

"Design Competition: Runners-Up for the Best Three Designs," EPN, vol. 26, No. 1, (2002).

"MiniMitter® Physiological and Behavioral Monitoring for Humans and Animals," http://www.minimitter.com/Products/Actiwatch, 3 pgs., (2006).

Notification of Transmittal of the International Preliminary Report on Patentability for corresponding PCT Application Serial No. PCT/US2005/008789, dated Mar. 16, 2006, 12 pgs.

Office Action dated Dec. 12, 2008 for U.S. Appl. No. 11/081,811 (12 pgs).

Office Action dated Nov. 6, 2008 for U.S. Appl. No. 11/081,857 (8 pgs).

Response dated Jan. 6, 2009 for U.S. Appl. No. 11/081,857 (6 pgs.).

* cited by examiner

| PARAMETER SET | PARAMETERS | SLEEP EFFICIENCY | SLEEP LATENCY | % OF TIME ACTIVE |
|---|---|---|---|---|
| 1 | PA = 5.5V<br>PW = 210ms<br>PR = 90Hz | 85% | 20 min. | 75%<br>(15% HIGH) |
| 2 | PA = 5V<br>PW = 190ms<br>PR = 95Hz | 75% | 25 min. | 60%<br>(5% HIGH) |
| ••• | | | | |
| N | PA = 4.6V<br>PW = 215ms<br>PR = 80Hz | 70% | 38 min. | 55%<br>(8% HIGH) |

FIG. 9

COLLECTING ACTIVITY AND SLEEP QUALITY INFORMATION VIA A MEDICAL DEVICE

This application claims the benefit of U.S. Provisional Application No. 60/553,785, filed Mar. 16, 2004, which is incorporated herein by reference in its entirety.

TECHNICAL FIELD

The invention relates to medical devices and, more particularly, to medical devices that monitor physiological parameters.

BACKGROUND

In some cases, an ailment may affect the quality of a patient's sleep and/or affect the patient's activity level. For example, chronic pain may cause a patient to have difficulty falling asleep, disturb the patient's sleep, e.g., cause the patient to wake, and prevent the patient from achieving deeper sleep states, such as one or more of the nonrapid eye movement (NREM) sleep states. Chronic pain may also cause a patient to avoid particular activities, or activity in general, where such activities increase the pain experienced by the patient. Other ailments that may negatively affect patient sleep quality and patient activity level include movement disorders, and congestive heart failure. In some cases, these ailments are treated via an implantable medical device (IMD), such as an implantable stimulator or drug delivery device.

Further, in some cases, poor sleep quality may increase the symptoms experienced by a patient due to an ailment. For example, poor sleep quality has been linked to increased pain symptoms in chronic pain patients. The link between poor sleep quality and increased symptoms is not limited to ailments that negatively impact sleep quality, such as those listed above. Nonetheless, the condition of a patient with such an ailment may progressively worsen when symptoms disturb sleep quality, which in turn increases the frequency and/or intensity of symptoms. The increased symptoms may, in turn, limit patient activity during the day, and further disturb sleep quality.

SUMMARY

In general, the invention is directed to techniques for collecting information that relates to patient activity and the quality of patient sleep via a medical device, such as an implantable medical device (IMD). The medical device determines whether to collect activity or sleep quality information by determining whether the patient is attempting to sleep. Activity and sleep quality information collected by the medical device may be presented to a user, such as a clinician, and used to, for example, evaluate the effectiveness of a therapy delivered to the patient by the medical device. For example, the activity and sleep quality information may be associated with different therapy parameter sets, permitting a user to evaluate relative efficacy of the therapy parameter sets.

The medical device may determine that the patient is attempting to sleep in a variety of ways. For example, the medical device may receive an indication from the patient that the patient is trying to fall asleep, e.g., via a patient programming device in embodiments in which the medical device is an implantable medical device. In other embodiments, the medical device may monitor the activity level of the patient, and identify the time that the patient is attempting to sleep by determining whether the patient has remained inactive for a threshold period of time and identifying the time at which the patient became inactive. In still other embodiments, the medical device may monitor patient posture, and identify the time when the patient is recumbent, e.g., lying down, as the time when the patient is attempting to fall asleep. In these embodiments, the medical device may also monitor patient activity, and confirm that the patient is attempting to sleep based on the patient's activity level.

As another example, the medical device may determine the time at which the patient begins attempting to fall asleep based on the level of melatonin within one or more bodily fluids, such as the patient's blood, cerebrospinal fluid (CSF), or interstitial fluid. The medical device may also determine a melatonin level based on metabolites of melatonin located in the saliva or urine of the patient. Melatonin is a hormone secreted by the pineal gland into the bloodstream and the CSF as a function of exposure of the optic nerve to light, which synchronizes the patient's circadian rhythm. In particular, increased levels of melatonin during evening hours may cause physiological changes in the patient, which, in turn, may cause the patient to attempt to fall asleep. The medical device may, for example, detect an increase in the level of melatonin, and estimate the time that the patient will attempt to fall asleep based on the detection.

When the medical device determines that the patient is attempting to sleep, the medical device may determine values for one or more metrics that indicate the quality of a patient's sleep based on at least one monitored physiological parameter of the patient. Example physiological parameters that the medical device may monitor to determine sleep quality metric values include activity level, posture, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and galvanic skin response. In order to monitor one or more of these parameters, the medical device may include, or be coupled to, one or more sensors, each of which generates a signal as a function of one or more of these physiological parameters. The medical device may determine a value of one or more sleep quality metrics based on the monitored physiological parameters, and/or the variability of one or more of the monitored physiological parameters.

Sleep efficiency and sleep latency are example sleep quality metrics for which a medical device may determine values. Sleep efficiency may be measured as the percentage of time while the patient is attempting to sleep that the patient is actually asleep, or actually within one of the different sleep states. Sleep latency may be measured as the amount of time between a first time when the patient begins attempting to fall asleep and a second time when the patient falls asleep, and thereby indicates how long a patient requires to fall asleep.

The time when the patient begins attempting to fall asleep may be determined in any of the variety of ways identified above. The time at which the patient has fallen asleep may be determined based on any one or more of the other physiological parameters that may be monitored by the medical device as indicated above. For example, a discernable change, e.g., a decrease, in one or more physiological parameters, or the variability of one or more physiological parameters, may indicate that the patient has fallen asleep. In some embodiments, the medical device determines a sleep probability metric value based on a value of a physiological parameter. In such embodiments, the medical device compares the sleep probability metric value to a threshold to identify when the patient has fallen asleep. In some embodiments, the medical device determines a plurality of sleep probability metric values based on a value of each of a plurality of physiological parameters, averages or otherwise combines the plurality of sleep probability metric values to provide an overall sleep probability metric value, and compares the overall sleep probability metric value to a threshold to identify the time that the patient falls asleep.

Other sleep quality metrics that the medical device may determine include total time sleeping per day, the amount or percentage of time sleeping during nighttime or daytime hours per day, and the number of apnea and/or arousal events per night. In some embodiments, the medical device may determine which sleep state the patient is in, e.g., rapid eye movement (REM), or one of the nonrapid eye movement (NREM) states (S1, S2, S3, S4) based on monitored physiological parameters, and the amount of time per day spent in these various sleep states may be determined by the medical device as a sleep quality metric. Because they provide the most "refreshing" type of sleep, the amount of time spent in one or both of the S3 and S4 sleep states, in particular, may be determined as a sleep quality metric. In some embodiments, the medical device may determine average or median values of one or more sleep quality metrics over greater periods of time, e.g., a week or a month, as the value of the sleep quality metric. Further, in embodiments in which values for a plurality of the sleep quality metrics are determined, the medical device may determine a value for an overall sleep quality metric based on the values for the plurality of individual sleep quality metrics.

When the device determines that the patient is not attempting to sleep, the device periodically determines activity levels of the patient. For example, the medical device may monitor a signal generated by an accelerometer, a bonded piezoelectric crystal, a mercury switch, or a gyro. In some embodiments, the medical device may monitor a signal that indicates a physiological parameter of the patient, which in turn varies as a function of patient activity. For example, the medical device may monitor a signal that indicates the heart rate, respiration rate, respiratory volume, or muscular activity of the patient.

The medical device may periodically determine an activity level of the patient based on the one or more signals. In some embodiments, the medical device periodically determines a number of activity counts based on the one or more signals, and the number of activity counts is stored as the activity level. The number of activity counts may be a number of threshold crossings by a signal generated by an accelerometer or piezoelectric crystal during a sample period, or a number of switch contacts indicated by the signal generated by a mercury switch during a sample period.

In some embodiments, the medical device may periodically determine a heart rate, respiration rate, respiratory volume, and/or muscular activity level of the patient based on one or more signals. The determined values of these parameters may be mean or median values. The medical device may compare a determined value of such a physiological parameter to one or more thresholds to determine a number of activity counts, which may be stored as a determined activity level. In other embodiments, the medical device may store the determined physiological parameter value as a determined activity level.

The use of activity counts, however, may allow the medical device to determine an activity level based on a plurality of signals. For example, the medical device may determine a first number of activity counts based on a sample of an accelerometer signal and a second number of activity counts based on a heart rate determined at the time the accelerometer signal was sampled. The medical device may determine an activity level by calculating the sum or average, which may be a weighted sum or average, of first and second activity counts.

The medical device may determine a value of one or more activity metrics based on determined activity levels. An activity metric value may be, for example, a mean or median activity level, such as an average number of activity counts per unit time. In other embodiments, an activity metric value may be chosen from a predetermined scale of activity metric values based on comparison of a mean or median activity level to one or more threshold values. The scale may be numeric, such as activity metric values from 1-10, or qualitative, such as low, medium or high activity.

In some embodiments, a number of collected activity levels are compared with one or more thresholds, and percentages of time above and/or below the thresholds are determined as one or more activity metric values. In other embodiments, a number of collected activity levels are compared with one or more thresholds, and an average length of time that consecutively determined activity levels remain above the threshold is determined as an activity metric value.

In some embodiments, the medical device delivers a therapy. At any given time, the medical device delivers the therapy according to a current set of therapy parameters. For example, in embodiments in which the medical device is a neurostimulator, a therapy parameter set may include a pulse amplitude, a pulse width, a pulse rate, a duty cycle, and an indication of active electrodes. Different therapy parameter sets may be selected, e.g., by the patient via a programming device or a the medical device according to a schedule, and parameters of one or more therapy parameter sets may be adjusted by the patient to create new therapy parameter sets. In other words, over time, the medical device delivers the therapy according to a plurality of therapy parameter sets.

When the medical device determines a sleep quality metric value or an activity level, the medical device may identify the current therapy parameter set when the value or level is determined, and may associate that value or level with the therapy parameter set. For each available therapy parameter set, the medical device may store a representative value of each of one or more sleep quality metrics in a memory with an indication of the therapy parameter set with which that representative value is associated. A representative value of sleep quality metric for a therapy parameter set may be the mean or median of collected sleep quality metric values that have been associated with that therapy parameter set. For each available therapy parameter set, the medical device may also store one or more associated activity metric values that are determined based on activity levels associated with that therapy parameter set.

A programming device according to the invention may be capable of wireless communication with the medical device, and may receive from the medical device information identifying the therapy parameter set, representative sleep quality metric values associated with the plurality of therapy parameter sets, and activity metric values associated with the therapy parameter sets. The programming device may display a list of the therapy parameter sets, which may be ordered according to any of the associated representative sleep quality metric values or activity metric values. A user may select the metric by which the list is ordered. Such a list may be used by a clinician to, for example, identify effective or ineffective therapy parameter sets.

In some embodiments, the medical device does not determine whether the patient is attempting to sleep, determine values for sleep quality metrics, determine activity metric values, and/or periodically determine activity levels. Instead, in some embodiments, a computing device, such as a programming device performs one or more of these functions. For example, a programming device may be used to program a medical device, and also receive physiological parameter values, activity levels, and/or samples of an activity signal from a medical device, and determine activity metric values and sleep quality metric values based on the information received from the medical device using any of the techniques described herein with reference to a medical device.

In some embodiments, the medical device may associate recorded physiological parameter values, signal samples, and/or activity levels with a current therapy parameter set, and may provide information identifying a plurality of therapy parameter sets and collected information associated with the therapy parameter sets to the programming device. In such embodiments, the programming device may determine representative sleep quality metric values and activity metric values associated with the various therapy parameter sets using any of techniques described herein with reference to a medical device. The programming device may receive such information from the medical device in real time, or may interrogate the medical device for information recorded by the medical device over a period of time.

In other embodiments, a system according to the invention does not include a programming device. For example, an external medical device according to the invention may include a display, collect sleep quality and activity information as described herein, and display sleep quality and activity information to a user via the display.

In one embodiment, the invention is directed to a method in which a plurality of physiological parameters of a patient are monitored via a medical device. The plurality of physiological parameters includes at least one physiological parameter indicative of patient physical activity. The method includes a determination of when the patient is attempting to sleep. Values of at least one metric that is indicative of sleep quality are determined based on at least one of the physiological parameters and a determination that the patient is attempting to sleep. An activity level of the patient is periodically determined based on at least one of the physiological parameters and a determination that the patient is not attempting to sleep.

In another embodiment, the invention is directed to a medical system including a medical device and a processor. The medical device monitors a plurality of physiological parameters of a patient, and the plurality of physiological parameters includes at least one physiological parameter indicative of patient physical activity. The processor determines when the patient is attempting to sleep, determines values of at least one metric that is indicative of sleep quality based on at least one of the physiological parameters and a determination that the patient is attempting to sleep, and periodically determines an activity level of the patient based on at least one of the physiological parameters and a determination that the patient is not attempting to sleep.

In another embodiment, the invention is directed to a medical system including means for monitoring a plurality of physiological parameters of a patient via a medical device, wherein the plurality of physiological parameters includes at least one physiological parameter indicative of patient physical activity, means for determining when the patient is attempting to sleep, means for determining values of at least one metric that is indicative of sleep quality based on at least one of the physiological parameters and a determination that the patient is attempting to sleep, and means for periodically determining an activity level of the patient based on at least one of the physiological parameters and a determination that the patient is not attempting to sleep.

In another embodiment, the invention is directed to a medical system including an implantable medical device and an external programming device that includes a display. The implantable medical device delivers a therapy to a patient based on a plurality of therapy parameter sets, monitors a plurality of physiological parameters of the patient including at least one physiological parameter indicative of patient physical activity, determines when the patient is attempting to sleep, determines values of at least one metric that is indicative of sleep quality based on at least one of the physiological parameters and a determination that the patient is attempting to sleep, periodically determines an activity level of the patient based on at least one of the physiological parameters and a determination that the patient is not attempting to sleep, associates each determined sleep quality metric value and each determined activity level with a current therapy parameter set, determines a representative value of each of the at least one sleep quality metrics for each of the plurality of therapy parameter sets based on the sleep quality metric values associated with the therapy parameter set, and determines at least one activity metric value for each of the plurality of therapy parameter sets based on the activity levels associated with the therapy parameter set. The external programming device receives information identifying the plurality of therapy parameter sets and the sleep quality metric values and activity metric values associated with the therapy parameter sets from the implantable medical device, and presents a list of the therapy parameter sets and the associated sleep quality metric values to a user.

In another embodiment, the invention is directed to a computer-readable medium comprising program instructions. The program instructions cause a programmable processor to monitor a plurality of physiological parameters of a patient, wherein the plurality of physiological parameters includes at least one physiological parameter indicative of patient physical activity, determine when the patient is attempting to sleep, determine values of at least one metric that is indicative of sleep quality based on at least one of the physiological parameters and a determination that the patient is attempting to sleep, and periodically determine an activity level of the patient based on at least one of the physiological parameters and a determination that the patient is not attempting to sleep.

The invention may be capable of providing one or more advantages. For example, by providing information related to patient activity and the quality of a patient's sleep to a clinician and/or the patient, a system according to the invention can improve the course of treatment of an ailment of the patient, such as chronic pain. For example, using activity and sleep quality information provided by the system, the clinician could evaluate a plurality of therapy parameter sets to identify those which are, or are not, efficacious.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 9 illustrates an example list of therapy parameter sets and associated sleep quality information and activity information that may be presented by a clinician programmer.

DETAILED DESCRIPTION

Figure 1:
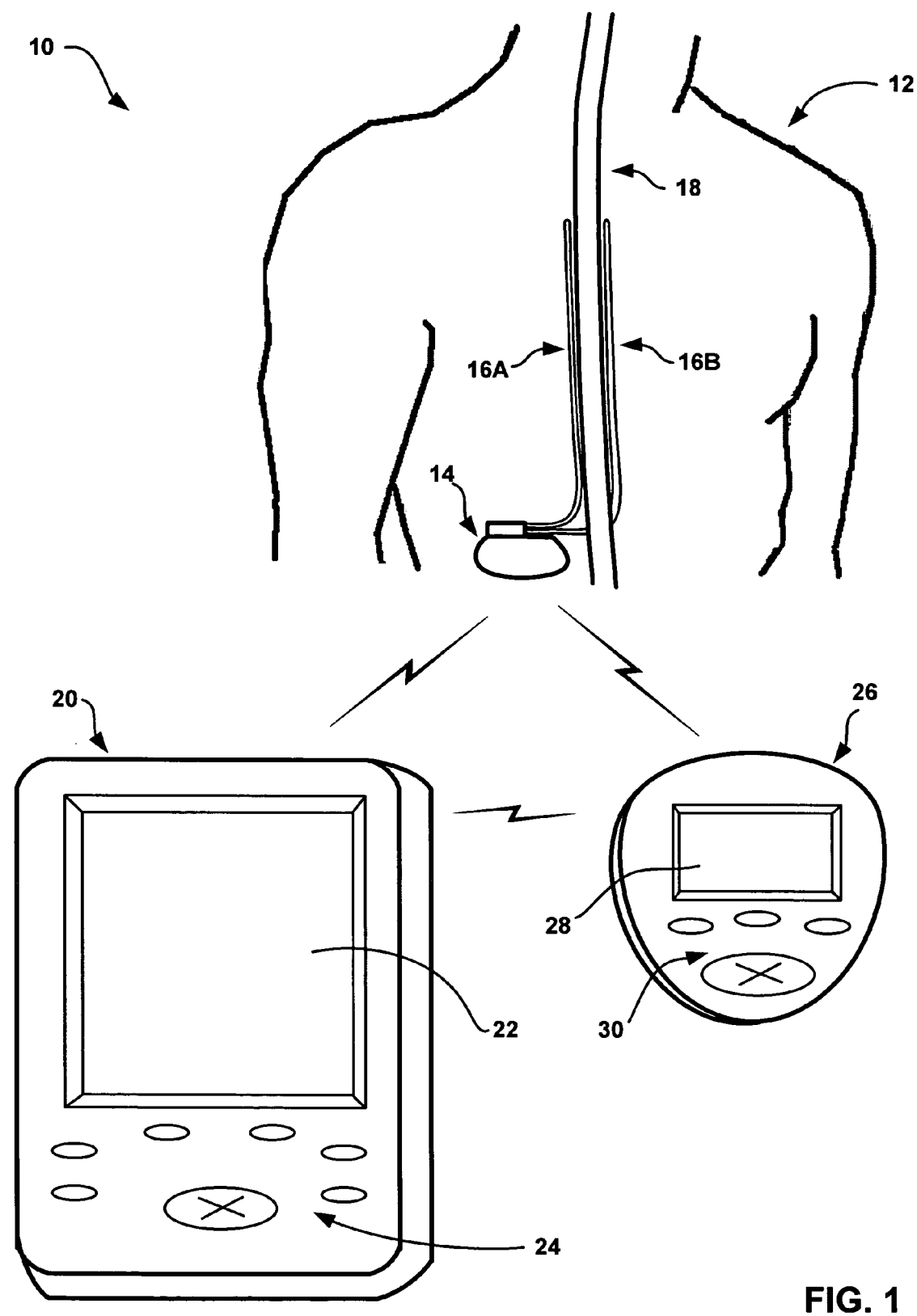
FIG. 1 is a conceptual diagram illustrating an example system that includes an implantable medical device that collects sleep quality information and activity information according to the invention.

FIG. 1 is a conceptual diagram illustrating an example system 10 that includes an implantable medical device (IMD) 14 that collects information relating to the quality of sleep experienced by a patient 12 and the activity of patient 12 according to the invention. Sleep quality information and activity information collected by IMD 14 is provided to a user, such as a clinician or the patient. Using the sleep quality information and activity information collected by IMD 14, a current course of therapy for an ailment of patient 12 may be evaluated, and an improved course of therapy for the ailment may be identified.

In the illustrated example system 10, IMD 14 takes the form of an implantable neurostimulator that delivers neurostimulation therapy in the form of electrical pulses to patient 12. However, the invention is not limited to implementation via an implantable neurostimulator. For example, in some embodiments of the invention, an implantable pump or implantable cardiac rhythm management device, such as a pacemaker may collect sleep quality information and activity information. Further, the invention is not limited to implementation via an IMD. In other words, any implantable or external medical device may collect sleep quality and activity information according to the invention.

In the example of FIG. 1, IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1 or the delivery of SCS therapy. For example, one or more leads 16 may extend from IMD 14 to the brain (not shown) of patient 12, and IMD 14 may deliver deep brain stimulation (DBS) therapy to patient 12 to, for example, treat tremor or epilepsy. As further examples, one or more leads 16 may be implanted proximate to the pelvic nerves (not shown) or stomach (not shown), and IMD 14 may deliver neurostimulation therapy to treat incontinence, sexual dysfunction or gastroparesis.

IMD 14 delivers therapy according to a set of therapy parameters, i.e., a set of values for a number of parameters that define the therapy delivered according to that therapy parameter set. In embodiments where IMD 14 delivers neurostimulation therapy in the form of electrical pulses, the parameters for each therapy parameter set may include voltage or current pulse amplitudes, pulse widths, pulse rates, and the like. Further, each of leads 16 includes electrodes (not shown in FIG. 1), and a therapy parameter set may include information identifying which electrodes have been selected for delivery of pulses, and the polarities of the selected electrodes. Therapy parameter sets used by IMD 14 may include a number of parameter sets programmed by a clinician (not shown), and parameter sets representing adjustments made by patient 12 to these preprogrammed sets.

System 10 also includes a clinician programmer 20. A clinician (not shown) may use clinician programmer 20 to program therapy for patient 12, e.g., specify a number of therapy parameter sets and provide the parameter sets to IMD 14. The clinician may also use clinician programmer 20 to retrieve information collected by IMD 14. The clinician may use clinician programmer 20 to communicate with IMD 14 both during initial programming of IMD 14, and for collection of information and further programming during follow-up visits.

Clinician programmer 20 may, as shown in FIG. 1, be a handheld computing device. Clinician programmer 20 includes a display 22, such as a LCD or LED display, to display information to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus or mouse. Keypad 24 may take the form of an alphanumeric keypad or a reduced set of keys associated with particular functions.

System 10 also includes a patient programmer 26, which also may, as shown in FIG. 1, be a handheld computing device. Patient 12 may use patient programmer 26 to control the delivery of therapy by IMD 14. For example, using patient programmer 26, patient 12 may select a current therapy parameter set from among the therapy parameter sets preprogrammed by the clinician, or may adjust one or more parameters of a preprogrammed therapy parameter set to arrive at the current therapy parameter set.

Patient programmer 26 may include a display 28 and a keypad 30, to allow patient 12 to interact with patient programmer 26. In some embodiments, display 28 may be a touch screen display, and patient 12 may interact with patient programmer 26 via display 28. Patient 12 may also interact with patient programmer 26 using peripheral pointing devices, such as a stylus, mouse, or the like.

However, clinician and patient programmers 20, 26 are not limited to the hand-held computer embodiments illustrated in FIG. 1. Programmers 20, 26 according to the invention may be any sort of computing device. For example, a programmer 20, 26 according to the invention may be a tablet-based computing device, a desktop computing device, or a workstation.

IMD 14, clinician programmer 20 and patient programmer 26 may, as shown in FIG. 1, communicate via wireless communication. Clinician programmer 20 and patient programmer 26 may, for example, communicate via wireless communication with IMD 14 using radio frequency (RF) or infrared telemetry techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols.

Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

As mentioned above, IMD 14 collects information that relates to the quality of sleep experienced by patient 12 and the activity of patient 12. In particular, as will be described in greater detail below, IMD 14 determines whether patient 12 is attempting to sleep, determines values for one or more sleep quality metrics when patient 12 is attempting to sleep, and periodically determines activity levels of patient 12 when patient 12 is not attempting to sleep, i.e., is more likely to be active. In some embodiments, IMD 14 determines values for one or more activity metrics based on the determined activity levels. IMD 14 may include or be coupled to one or more sensors (not shown in FIG. 1), each of which generates a signal as a function of one or more of these physiological parameters, and may determine sleep quality metrics and activity levels based on the signals output by the sensors.

At any given time, as indicated above, IMD 14 delivers the therapy according to a current set of therapy parameters. Different therapy parameter sets may be selected, e.g., by patient 12 via patient programmer 26 or IMD 14 according to a schedule, and parameters of one or more therapy parameter sets may be adjusted by patient 12 via patient programmer 26 to create new therapy parameter sets. In other words, over time, IMD 14 delivers the therapy according to a plurality of therapy parameter sets.

In some embodiments, as will be described in greater detail below, IMD 14 identifies the therapy parameter set currently used to deliver therapy to patient 12 when a value of a sleep quality metric or an activity level is determined, and may associate the determined values and levels with current therapy parameter sets. For each of the plurality of therapy parameter sets, IMD 14 may store a representative value of each of one or more sleep quality metrics in a memory with an indication of the therapy parameter set with which that representative value is associated. A representative value of a sleep quality metric for a therapy parameter set may be the mean or median of collected sleep quality metric values that have been associated with that therapy parameter set. For each available therapy parameter set, IMD 14 may also store one or more associated activity metric values that are determined based on activity levels associated with that therapy parameter set.

A programming device, such as clinician programmer 20, may receive information identifying the therapy parameter set, representative sleep quality metric values associated with the plurality of therapy parameter sets, and activity metric values associated with the therapy parameter sets from IMD 14. Clinician programmer 20 may display a list of the therapy parameter sets, which may be ordered according to any of the associated representative sleep quality metric values or activity metric values. A clinician may select the metric by which the list is ordered. Such a list may be used by the clinician to, for example, identify effective or ineffective therapy parameter sets.

Figure 2:
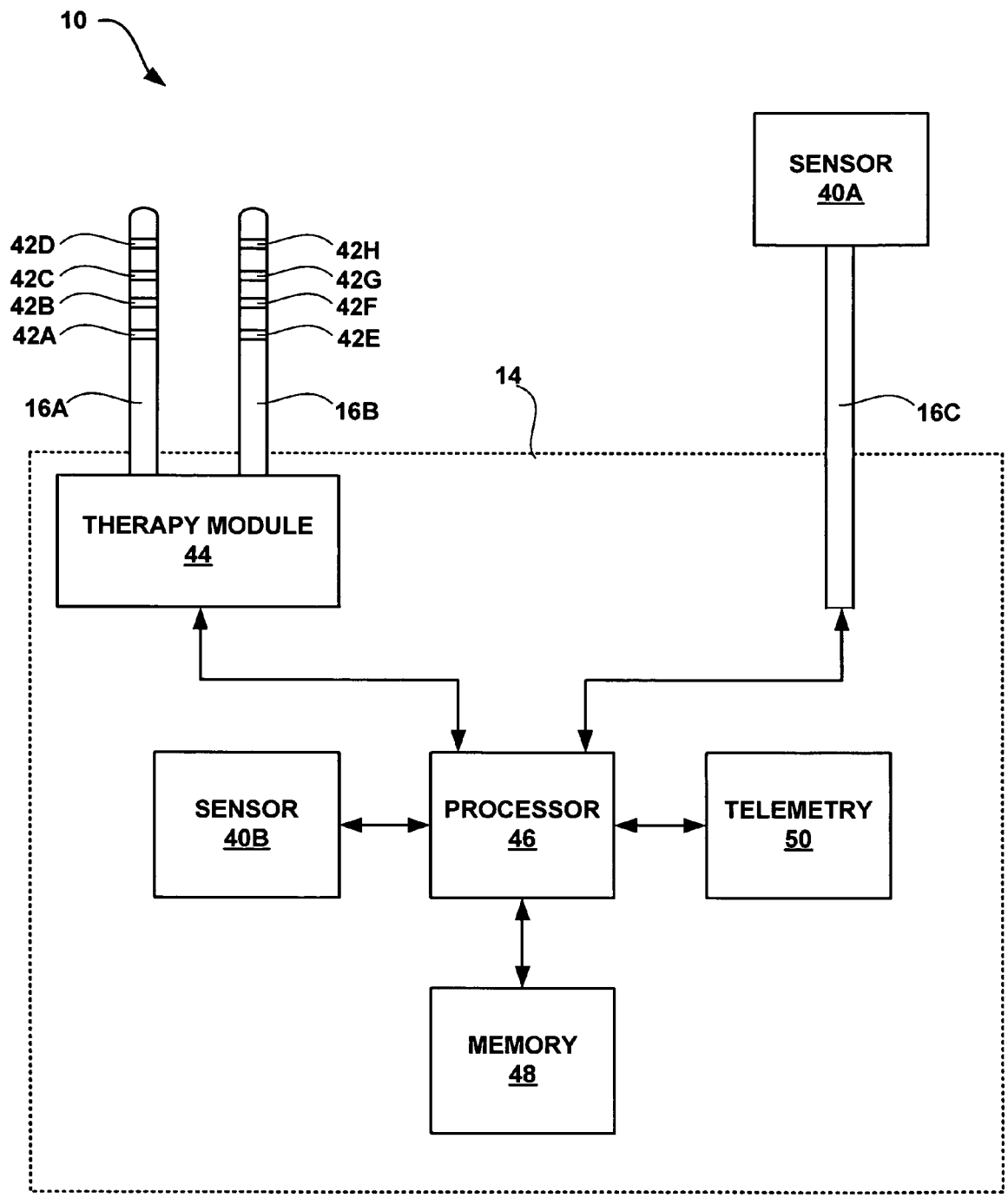
FIG. 2 is a block diagram further illustrating the example system and implantable medical device of FIG. 1.

FIG. 2 is a block diagram further illustrating system 10. In particular, FIG. 2 illustrates an example configuration of IMD 14 and leads 16A and 16B. FIG. 2 also illustrates sensors 40A and 40B (collectively "sensors 40") that generate signals as a function of one or more physiological parameters of patient 12. As will be described in greater detail below, IMD 14 monitors at least some of the signals to determine values for one or more metrics that are indicative of sleep quality when the patient is attempting to sleep, and monitors at least some of the signals to determine activity levels of patient 12 when the patient is not attempting to sleep.

IMD 14 may deliver neurostimulation therapy via electrodes 42A-D of lead 16A and electrodes 42E-H of lead 16B (collectively "electrodes 42"). Electrodes 42 may be ring electrodes. The configuration, type and number of electrodes 42 illustrated in FIG. 2 are merely exemplary. For example, leads 16A and 16B may each include eight electrodes 42, and the electrodes 42 need not be arranged linearly on each of leads 16A and 16B.

Electrodes 42 are electrically coupled to a therapy delivery module 44 via leads 16A and 16B. Therapy delivery module 44 may, for example, include an output pulse generator coupled to a power source such as a battery. Therapy delivery module 44 may deliver electrical pulses to patient 12 via at least some of electrodes 42 under the control of a processor 46, which controls therapy delivery module 44 to deliver neurostimulation therapy according to to a current therapy parameter set. However, the invention is not limited to implantable neurostimulator embodiments or even to IMDs that deliver electrical stimulation. For example, in some embodiments, a therapy delivery module 44 of an IMD may include a pump, circuitry to control the pump, and a reservoir to store a therapeutic agent for delivery via the pump.

Processor 46 may include a microprocessor, a controller, a digital signal processor (DSP), an application specific integrated circuit (ASIC), a field-programmable gate array (FPGA), discrete logic circuitry, or the like. Memory 48 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. In some embodiments, memory 48 stores program instructions that, when executed by processor 46, cause IMD 14 and processor 46 to perform the functions attributed to them herein.

Each of sensors 40 generates a signal as a function of one or more physiological parameters of patient 12. IMD 14 may include circuitry (not shown) that conditions the signals generated by sensors 40 such that they may be analyzed by processor 46. For example, IMD 14 may include one or more analog to digital converters to convert analog signals generated by sensors 40 into digital signals usable by processor 46, as well as suitable filter and amplifier circuitry. Although shown as including two sensors 40, system 10 may include any number of sensors.

Further, as illustrated in FIG. 2, sensors 40 may be included as part of IMD 14, or coupled to IMD 14 via leads 16. Sensors 40 may be coupled to IMD 14 via therapy leads 16A and 16B, or via other leads 16, such as lead 16C depicted in FIG. 2. In some embodiments, a sensor 40 located outside of IMD 14 may be in wireless communication with processor 46.

Exemplary physiological parameters of patient 12 that may be monitored by IMD 14 include activity, posture, heart rate, respiration rate, respiratory volume, blood pressure, blood oxygen saturation, partial pressure of oxygen within blood, partial pressure of oxygen within cerebrospinal fluid (CSF), muscular activity, core temperature, arterial blood flow, and the level of melatonin within one or more bodily fluids. Further, as discussed above, in some external medical device embodiments of the invention, galvanic skin response may additionally or alternatively be monitored. Sensors 40 may be of any type known in the art capable of generating a signal as a function of one or more of these parameters.

Processor 46 may identify when patient 12 is attempting to sleep in a variety of ways. For example, processor 46 may identify the time that patient begins attempting to fall asleep based on an indication received from patient 12, e.g., via clinician programmer 20 and a telemetry circuit 50. In other embodiments, processor 46 identifies the time that patient 12 begins attempting to fall asleep based on the activity level of patient 12.

In such embodiments, IMD 14 may include one or more sensors 40 that generate a signal as a function of patient activity. For example, sensors 40 may include one or more accelerometers, gyros, mercury switches, or bonded piezoelectric crystals that generates a signal as a function of patient activity, e.g., body motion, footfalls or other impact events, and the like. Processor 46 may identify a time when the activity level of patient 12 falls below a threshold activity level value stored in memory 48, and may determine whether the activity level remains substantially below the threshold activity level value for a threshold amount of time stored in memory 48. In other words, patient 12 remaining inactive for a sufficient period of time may indicate that patient 12 is attempting to fall asleep. If processor 46 determines that the threshold amount of time is exceeded, processor 46 may identify the time at which the activity level fell below the threshold activity level value as the time that patient 12 began attempting to fall asleep.

In some embodiments, processor 46 determines whether patient 12 is attempting to fall asleep based on whether patient 12 is or is not recumbent, e.g., lying down. In such embodiments, sensors 40 may include a plurality of accelerometers, gyros, or magnetometers oriented orthogonally that generate signals which indicate the posture of patient 12. In addition to being oriented orthogonally with respect to each other, each of sensors 40 used to detect the posture of patient 12 may be generally aligned with an axis of the body of patient 12. In exemplary embodiments, IMD 14 includes three orthogonally oriented posture sensors 40.

When sensors 40 include accelerometers, for example, that are aligned in this manner, processor 46 may monitor the magnitude and polarity of DC components of the signals generated by the accelerometers to determine the orientation of patient 12 relative to the Earth's gravity, e.g., the posture of patient 12. In particular, the processor 46 may compare the DC components of the signals to respective threshold values stored in memory 48 to determine whether patient 12 is or is not recumbent. Further information regarding use of orthogonally aligned accelerometers to determine patient posture may be found in a commonly assigned U.S. Pat. No. 5,593,431, which issued to Todd J. Sheldon.

In some embodiments, processor 46 considers both the posture and the activity level of patient 12 when determining whether patient 12 is attempting to fall asleep. For example, processor 46 may determine whether patient 12 is attempting to fall asleep based on a sufficiently long period of sub-threshold activity, as described above, and may identify the time that patient began attempting to fall asleep as the time when patient 12 became recumbent. Any of a variety of combinations or variations of these techniques may be used to determine when patient 12 is attempting to fall asleep, and a specific one or more techniques may be selected based on the sleeping and activity habits of a particular patient.

In other embodiments, processor 46 determines when patient 12 is attempting to fall asleep based on the level of melatonin in a bodily fluid. In such embodiments, a sensor 40 may take the form of a chemical sensor that is sensitive to the level of melatonin or a metabolite of melatonin in the bodily fluid, and estimate the time that patient 12 will attempt to fall asleep based on the detection. For example, processor 46 may compare the melatonin level or rate of change in the melatonin level to a threshold level stored in memory 48, and identify the time that threshold value is exceeded. Processor 46 may identify the time that patient 12 is attempting to fall asleep as the time that the threshold is exceeded, or some amount of time after the threshold is exceeded. Any of a variety of combinations or variations of the above-described techniques may be used to determine when patient 12 is attempting to fall asleep, and a specific one or more techniques may be selected based on the sleeping and activity habits of a particular patient.

When IMD 14 determines that patient 12 is attempting to sleep, IMD 14 may determine values for one or more metrics that indicate the quality of a patient's sleep based on at least one of the above-identified physiological parameters of the patient. In particular, in order to determine values for some sleep quality metrics, IMD 14 determines when patient 12 is asleep, e.g., identify the times that patient 12 falls asleep and wakes up, in addition to when patient 12 is attempting to fall asleep. The detected values of physiological parameters of patient 12, such as activity level, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and galvanic skin response may discernibly change when patient 12 falls asleep or awakes. In particular, these physiological parameters may be at low values when patient 12 is asleep. Further, the variability of at least some of these parameters, such as heart rate and respiration rate, may be at a low value when the patient is asleep.

Consequently, in order to detect when patient 12 falls asleep and wakes up, processor 46 may monitor one or more of these physiological parameters, or the variability of these physiological parameters, and detect the discernable changes in their values associated with a transition between a sleeping state and an awake state. In some embodiments, processor 46 may determine a mean or median value for a parameter based on values of a signal over time, and determine whether patient 12 is asleep or awake based on the mean or median value. Processor 46 may compare one or more parameter or parameter variability values to thresholds stored in memory 48 to detect when patient 12 falls asleep or awakes. The thresholds may be absolute values of a physiological parameter, or time rate of change values for the physiological parameter, e.g., to detect sudden changes in the value of a parameter or parameter variability. In some embodiments, a threshold used by processor 46 to determine whether patient 12 is asleep may include a time component. For example, a threshold may require that a physiological parameter be above or below a threshold value for a period of time before processor 46 determines that patient is awake or asleep.

In some embodiments, in order to determine whether patient 12 is asleep, processor 46 monitors a plurality of physiological parameters, and determines a value of a metric that indicates the probability that patient 12 is asleep for each of the parameters based on a value of the parameter. In particular, the processor 46 may apply a function or look-up table to the current, mean or median value, and/or the variability of each of a plurality of physiological parameters to determine a sleep probability metric for each of the plurality of physiological parameters. A sleep probability metric value may be a numeric value, and in some embodiments may be a probability value, e.g., a number within the range from 0 to 1, or a percentage value.

Processor 46 may average or otherwise combine the plurality of sleep probability metric values to provide an overall sleep probability metric value. In some embodiments, processor 46 may apply a weighting factor to one or more of the sleep probability metric values prior to combination. Processor 46 may compare the overall sleep probability metric value to one or more threshold values stored in memory 48 to determine when patient 12 falls asleep or awakes. Use of sleep probability metric values to determine when a patient is asleep based on a plurality of monitored physiological parameters is described in greater detail in a commonly-assigned and copending U.S. patent application No. 60/553,771 by Ken Heruth and Keith Miesel, entitled "DETECTING SLEEP," and filed on Apr. 15, 2004, which is incorporated herein by reference in its entirety.

To enable processor 46 to determine when patient 12 is asleep or awake, sensors 40 may include, for example, activity sensors as described above. As another example, sensors 40 may include electrodes located on leads or integrated as part of the housing of IMD 14 that generate an electrogram signal as a function of electrical activity of the heart of patient 12, and processor 46 may monitor the heart rate of patient 12 based on the electrogram signal. In other embodiments, a sensor may include an acoustic sensor within IMD 14, a pressure or flow sensor within the bloodstream or cerebrospinal fluid of patient 12, or a temperature sensor located within the bloodstream of patient 12. The signals generated by such sensors may vary as a function of contraction of the heart of patient 12, and can be used by IMD 14 to monitor the heart rate of patient 12.

In some embodiments, sensors 40 may include an electrode pair, including one electrode integrated with the housing of IMD 14 and one of electrodes 42, that generates a signal as a function of the thoracic impedance of patient 12, which varies as a function of respiration by patient 12. In other embodiments, sensors 40 may include a strain gauge, bonded piezoelectric element, or pressure sensor within the blood or cerebrospinal fluid that generates a signal that varies based on patient respiration. An electrogram generated by electrodes as discussed above may also be modulated by patient respiration, and may be used as an indirect representation of respiration rate.

Sensors 40 may include electrodes that generate an electromyogram (EMG) signal as a function of muscle electrical activity, or may include any of a variety of known temperature sensors to generate a signal as a function of a core temperature of patient 12. Such electrodes and temperature sensors may be incorporated within the housing of IMD 14, or coupled to IMD 14 via leads. Sensors 40 may also include a pressure sensor within, or in contact with, a blood vessel. The pressure sensor may generate a signal as a function of the a blood pressure of patient 12, and may, for example, comprise a Chronicle Hemodynamic Monitor™ commercially available from Medtronic, Inc. of Minneapolis, Minn.

Sensors 40 may also include optical pulse oximetry sensors or Clark dissolved oxygen sensors located within, as part of a housing of, or outside of IMD 14, which generate signals as a function of blood oxygen saturation and blood oxygen partial pressure respectively. In some embodiments, system 10 may include a catheter with a distal portion located within the cerebrospinal fluid of patient 12, and the distal end may include a Clark dissolved oxygen sensor to generate a signal as a function of the partial pressure of oxygen within the cerebrospinal fluid. Embodiments in which an IMD comprises an implantable pump, for example, may include a catheter with a distal portion located in the cerebrospinal fluid.

In some embodiments, sensors 40 may include one or more intraluminal, extraluminal, or external flow sensors positioned to generate a signal as a function of arterial blood flow. A flow sensor may be, for example, an electromagnetic, thermal convection, ultrasonic-Doppler, or laser-Doppler flow sensor. Further, in some external medical device embodiments of the invention, sensors 40 may include one or more electrodes positioned on the skin of patient 12 to generate a signal as a function of galvanic skin response.

Processor 46 may also detect arousals and/or apneas that occur when patient 12 is asleep based on one or more of the above-identified physiological parameters. For example, processor 46 may detect an arousal based on an increase or sudden increase in one or more of heart rate, heart rate variability, respiration rate, respiration rate variability, blood pressure, or muscular activity as the occurrence of an arousal. Processor 46 may detect an apnea based on a disturbance in the respiration rate of patient 12, e.g., a period with no respiration. Memory 48 may store thresholds used by processor 46 to detect arousals and apneas. Processor 46 may determine, as a sleep quality metric value, the number of apnea events and/or arousals during a night.

Further, in some embodiments, processor 46 may determine which sleep state patient 12 is in during sleep, e.g., REM, S1, S2, S3, or S4, based on one or more of the monitored physiological parameters. In particular, memory 48 may store one or more thresholds for each of sleep states, and processor 46 may compare physiological parameter or sleep probability metric values to the thresholds to determine which sleep state patient 12 is currently in. Processor 46 may determine, as sleep quality metric values, the amounts of time per night spent in the various sleep states.

The S3 and S4 sleep states may be of particular importance to the quality of sleep experienced by patient 12. Interruption from reaching these states, or inadequate time per night spent in these states, may cause patient 12 to not feel rested. For this reason, the S3 and S4 sleep states are believed to provide the "refreshing" part of sleep.

In some cases, interruption from reaching the S3 and S4 sleep states, or inadequate time per night spent in these states has been demonstrated to cause normal subjects to exhibit some symptoms of fibromyalgia. Also, subjects with fibromyalgia usually do not reach these sleep states. For these reasons, in some embodiments, IMD 14 may determine an amount or percentage of time spent in one or both of the S3 and S4 sleep states as a sleep quality metric.

When processor 46 determines that patient 12 is not attempting to sleep, processor 46 periodically determines activity levels of the patient. For example, a sensor 40 may be an accelerometer, a bonded piezoelectric crystal, a mercury switch, or a gyro, and processor 46 may determine an activity level based on a signal generated by one of these types of sensors 40 by sampling the signal and determining a number of activity counts during the sample period. Processor 46 may then store the determined number of activity counts in memory 48 as an activity level.

For example, processor 46 may compare the sample of a signal generated by an accelerometer or piezoelectric crystal to one or more amplitude thresholds stored within memory 48. Processor 46 may identify each threshold crossing as an activity count. Where processor 46 compares the sample to multiple thresholds with varying amplitudes, processor 46 may identify crossing of higher amplitude thresholds as multiple activity counts. Using multiple thresholds to identify activity counts, processor 46 may be able to more accurately determine the extent of patient activity for both high impact, low frequency and low impact, high frequency activities. In embodiments in which a sensor 40 takes the form of a mercury switch, processor 46 may identify the number of switch contacts indicated during the sample period as the number of activity counts.

In embodiments in which a sensor 40 comprises an accelerometer or piezoelectric crystal, IMD 14 may include a filter (not shown), or processor 46 may apply a digital filter, that passes a band from approximately 0.1 Hz to 10 Hz. The filter may reduce noise in the signal, and pass the portion of the signal that reflects patient activity.

In some embodiments, the processor 46 may monitor a signal that indicates a physiological parameter of patient 12, which in turn varies as a function of patient activity. For example, in some embodiments, sensors 40 may includes one or more sensors that generate a signal that indicates the heart rate, respiration rate, respiratory volume, or muscular activity of the patient, as described above. In such embodiments, processor 46 may periodically determine the heart rate, respiration rate, respiratory volume, or muscular activity level of patient 12 based on the signal. The determined values of these parameters may be mean or median values.

In some embodiments, processor 46 compares a determined value of such a physiological parameter to one or more thresholds or a look-up table stored in memory to determine a number of activity counts, and stores the determined number of activity counts in memory 48 as a determined activity level. In other embodiments, processor 46 may store the determined physiological parameter value as a determined activity level. The use of activity counts, however, may allow processor 46 to determine an activity level based on a plurality of signals generated by a plurality of sensors 40. For example, processor 46 may determine a first number of activity counts based on a sample of an accelerometer signal and a second number of activity counts based on a heart rate determined from an electrogram signal at the time the accelerometer signal was sampled. Processor 46 may determine an activity level by calculating the sum or average, which may be a weighted sum or average, of first and second activity counts.

Processor 46 may record activity levels continuously or periodically, e.g., one sample every minute or continuously for ten minutes each hour. Further processor 46 need not determine sleep quality metrics each time patient 12 attempts to sleep, or record activity levels each time patient 12 is not attempting to sleep. In some embodiments, processor 46 may record activity levels and determine sleep quality metric values in response to receiving an indication from patient 12 via patient programmer 26. Patient 12 may provide the indication by depressing a button or otherwise manipulating user input media on programmer 26. For example, processor 46 may record activity levels and sleep quality metrics during times when patient 12 believes the therapy delivered by IMD 14 is ineffective and/or the symptoms experienced by patient 12 have worsened. In this manner, processor 46 may limit data collection to periods in which more probative data is likely to be collected, and thereby conserve a battery and/or storage space within memory 48.

In some embodiments, processor 46 determines a value of one or more activity metrics based on determined activity levels and stores the activity metric values within memory 48. For example, processor 46 may determine a mean or median of activity levels, and store the mean or median activity level as an activity metric value. In embodiments in which activity levels comprise activity counts, processor 46 may store, for example, an average number of activity counts per unit time as an activity metric value.

In other embodiments, processor 46 may compare a mean or median activity level to one or more threshold values, and may select an activity metric value from a predetermined scale of activity metric values based on the comparison. The scale may be numeric, such as activity metric values from 1-10, or qualitative, such as low, medium or high activity. The scale of activity metric values may be, for example, stored as a look-up table within memory 48. Processor 46 stores the activity metric value selected from the scale within memory 48.

In some embodiments, processor 46 compares a number of activity levels to one or more threshold values. Based on the comparison, processor 46 may determine percentages of time above and/or below the thresholds, or within threshold ranges. Processor 46 may store the determined percentages within memory 48 as one or more activity metric values. In other embodiments, processor 46 compares a number of activity levels to a threshold value, and determines an average length of time that consecutively recorded activity levels remained above the threshold as an activity metric value.

Figure 3:
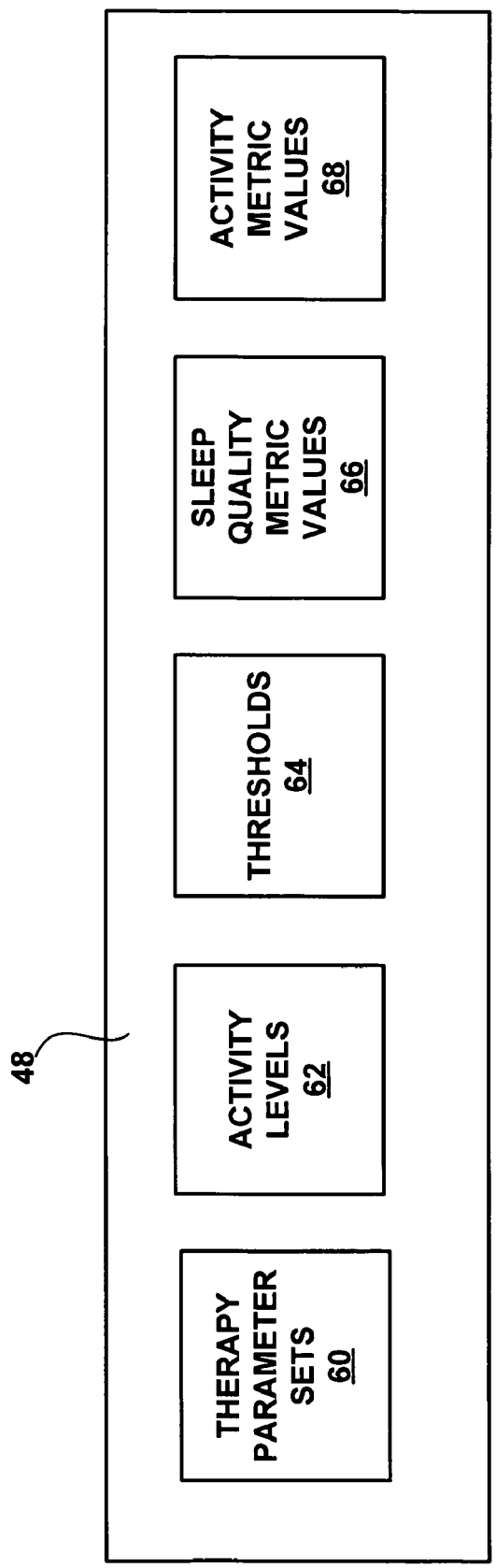
FIG. 3 is a block diagram illustrating an example memory of the implantable medical device of FIG. 1.

FIG. 3 further illustrates memory 48 of IMD 14. As illustrated in FIG. 3, memory 48 stores information describing a plurality of therapy parameter sets 60. Therapy parameter sets 60 may include parameter sets specified by a clinician using clinician programmer 20. Therapy parameter sets 60 may also include parameter sets that are the result of patient 12 changing one or more parameters of one of the preprogrammed therapy parameter sets.

Memory 48 also stores the activity levels 62, sleep quality metric values 66, and activity metric values 68 determined by processor 46, as described herein, and threshold values 64 used by processor 46 to determine activity levels 62, sleep quality metric values 66, and activity metric values 68, as described herein. In some embodiments, memory 48 also stores one or more functions or look-up tables (not shown) used by processor 46 to determine sleep probability metric values, activity levels 62, sleep quality metric values 66, and activity metric values 68, as described herein.

Processor 46 may store each sleep quality metric value determined within memory 48 as a sleep quality metric value 66, or may store mean or median sleep quality metric values over periods of time such as days, weeks or months as sleep quality metric values 66. Further, processor 46 may apply a function or look-up table to a plurality of sleep quality metric values to determine overall sleep quality metric value, and may store the overall sleep quality metric values within memory 48. The application of a function or look-up table by processor 46 for this purpose may involve the use or weighting factors for one or more of the individual sleep quality metric values.

Similarly, in some embodiments, processor 46 determines a plurality of activity metric values, and determines an overall activity metric value for a parameter set based on the values of the individual activity metrics for that parameter set. For example, processor 46 may use the plurality of individual activity metric values as indices to identify an overall activity metric value from a look-up table stored in memory 48. Processor 46 may select the overall metric value from a predetermined scale of activity metric values, which may be numeric, such as activity metric values from 1-10, or qualitative, such as low, medium or high activity.

In some embodiments, processor 46 identifies which of therapy parameter sets 60 is currently selected for use in delivering therapy to patient 12 when an activity level 62 or sleep quality metric value 66 is collected, and may associate that value or level with the current therapy parameter set. For example, for each of the plurality of therapy parameter sets 60, processor 46 may store a representative value of each of one or more sleep quality metrics within memory 48 as a sleep quality metric value 66 with an indication of the therapy parameter set with which that representative value is associated. A representative value of sleep quality metric for a therapy parameter set may be the mean or median of collected sleep quality metric values that have been associated with that therapy parameter set. Further, processor 46 may determine a value of one or more activity metrics for each of therapy parameter sets 60 based on activity levels 62 associated with that therapy parameter set, and may store the associated activity metric values 68 within memory 48.

As shown in FIG. 2, IMD 14 also includes a telemetry circuit 50 that allows processor 46 to communicate with clinician programmer 20 and patient programmer 26. Processor 46 may receive information identifying therapy parameter sets 60 preprogrammed by the clinician and threshold values 64 from clinician programmer 20 via telemetry circuit 50 for storage in memory 48. Processor 46 may receive an indication of the therapy parameter set 60 selected by patient 12 for delivery of therapy, or adjustments to one or more of therapy parameter sets 60 made by patient 12, from patient programmer 26 via telemetry circuit 50. Programmers 20, 26 may receive sleep quality metric values 66 and activity metric values 68 from processor 46 via telemetry circuit 50.

Figure 4:
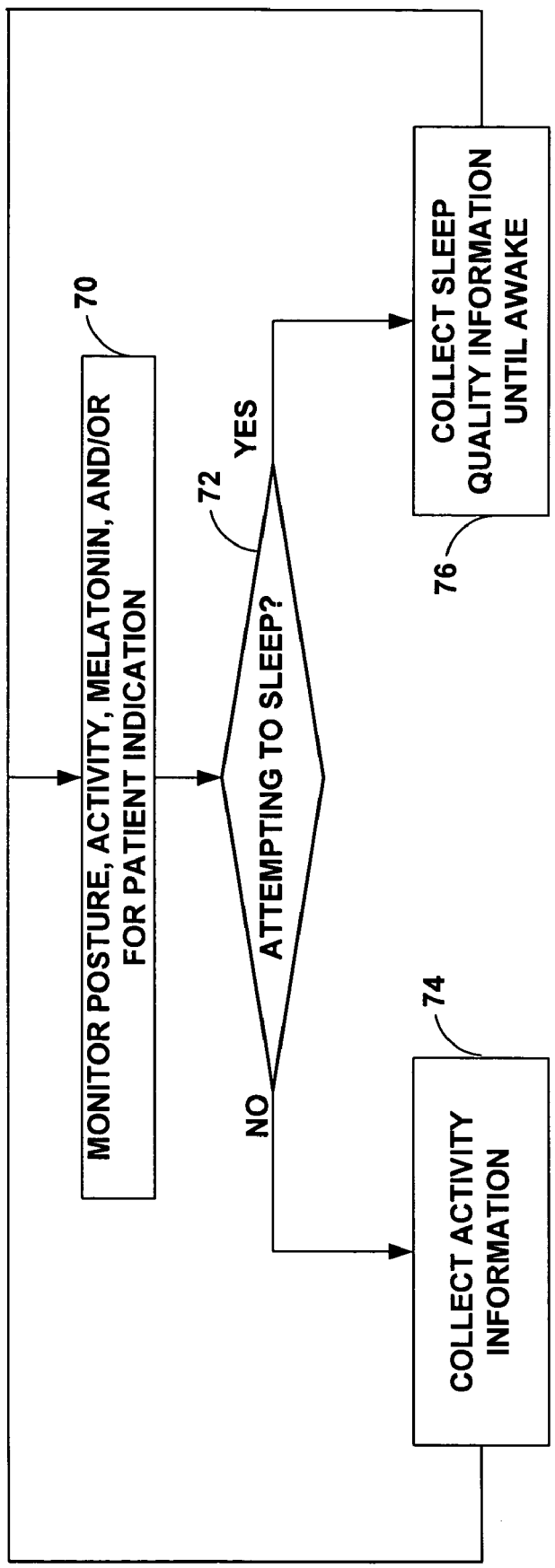
FIG. 4 is a flow diagram illustrating an example method for collecting sleep quality information and activity information that may be employed by an implantable medical device.

FIG. 4 is a flow diagram illustrating an example method for collecting sleep quality information and activity information that may be employed by IMD 14. IMD 14 monitors the posture, activity level, and/or melatonin level of patient 12, or monitors for an indication from patient 12, e.g., via patient programmer 26 (70), and determines whether patient 12 is attempting to fall asleep based on the posture, activity level, and/or a patient indication, as described above (72). When IMD 14 determines that patient 12 is not attempting to fall asleep, IMD 14 collects activity information, e.g., periodically determines activity levels 62 (74). When IMD 14 determines that patient 12 is attempting to fall asleep, IMD 14 collects sleep quality information, e.g., determines sleep quality metric values, until patient 12 is determined to be awake (76).

As discussed above, IMD 14 need not collect sleep information each time patient 12 attempts to sleep, or record activity levels each time patient 12 is not attempting to sleep. In some embodiments, IMD 14 may record activity levels and determine sleep quality metric values in response to receiving an indication from patient 12 via patient programmer 26. For example, IMD 14 may record activity levels and sleep quality metrics during times when patient 12 believes the therapy delivered by IMD 14 is ineffective and/or the symptoms experienced by patient 12 have worsened. In this manner, IMD 14 may limit data collection to periods in which more probative data is likely to be collected, and thereby conserve a battery and/or storage space within memory 48.

Figure 5:
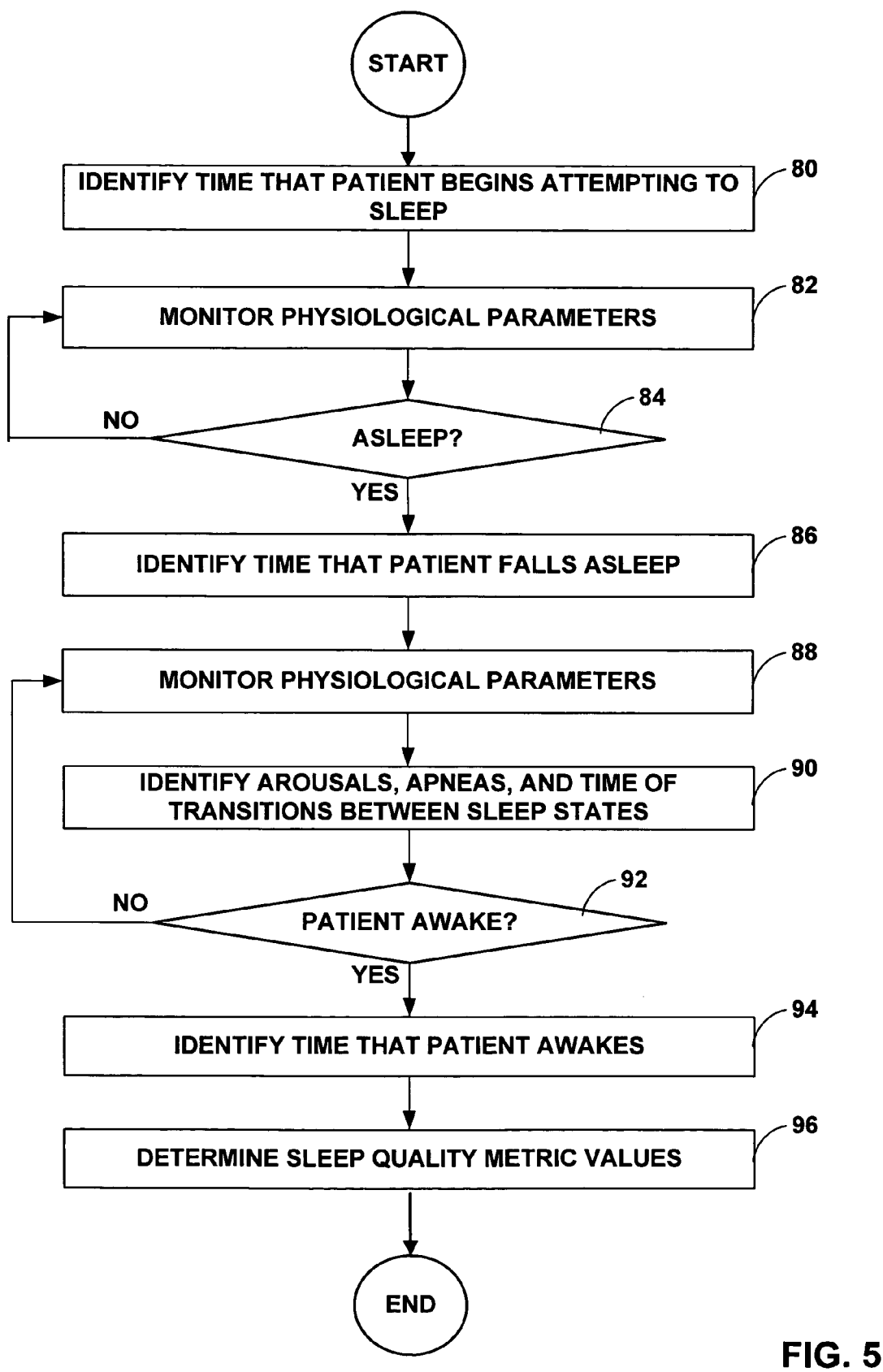
FIG. 5 is a flow diagram illustrating an example method for collecting sleep quality information that may be employed by an implantable medical device.

FIG. 5 is a flow diagram illustrating an example method for collecting sleep quality information that may be employed by IMD 14. When IMD 14 determines that patient 12 is attempting to fall asleep (FIG. 4), IMD 14 identifies the time that patient 12 began attempting to fall asleep using any of the techniques described above (80), and monitors one or more of the various physiological parameters of patient 12 discussed above to determine whether patient 12 is asleep (82, 84).

In some embodiments, IMD 14 compares parameter values or parameter variability values to one or more threshold values 64 to determine whether patient 12 is asleep. In other embodiments, IMD 14 applies one or more functions or look-up tables to determine one or more sleep probability metric values based on the physiological parameter values, and compares the sleep probability metric values to one or more threshold values 64 to determine whether patient 12 is asleep. While monitoring physiological parameters (82) to determine whether patient 12 is asleep (84), IMD 14 may continue to monitor the posture and/or activity level of patient 12 to confirm that patient 12 is still attempting to fall asleep.

When IMD 14 determines that patient 12 is asleep, e.g., by analysis of the various parameters contemplated herein, IMD 14 will identify the time that patient 12 fell asleep (86). While patient 12 is sleeping, IMD 14 will continue to monitor physiological parameters of patient 12 (88). As discussed above, IMD 14 may identify the occurrence of arousals and/or apneas based on the monitored physiological parameters (90). Further, IMD 14 may identify the time that transitions between sleep states, e.g., REM, S1, S2, S3, and S4, occur based on the monitored physiological parameters (90).

Additionally, while patient 12 is sleeping, IMD 14 monitors physiological parameters of patient 12 (88) to determine whether patient 12 has woken up (92). When IMD 14 determines that patient 12 is awake, IMD 14 identifies the time that patient 12 awoke (94), and determines sleep quality metric values based on the information collected while patient 12 was asleep (96).

For example, one sleep quality metric value IMD 14 may calculate is sleep efficiency, which IMD 14 may calculate as a percentage of time during which patient 12 is attempting to sleep that patient 12 is actually asleep. IMD 14 may determine a first amount of time between the time IMD 14 identified that patient 12 fell asleep and the time IMD 14 identified that patient 12 awoke. IMD may also determine a second amount of time between the time IMD 14 identified that patient 12 began attempting to fall asleep and the time IMD 14 identified that patient 12 awoke. To calculate the sleep efficiency, IMD 14 may divide the first time by the second time.

Another sleep quality metric value that IMD 14 may calculate is sleep latency, which IMD 14 may calculate as the amount of time between the time IMD 14 identified that patient 12 was attempting to fall asleep and the time IMD 14 identified that patient 12 fell asleep. Other sleep quality metrics with values determined by IMD 14 based on the information collected by IMD 14 in the illustrated example include: total time sleeping per day, at night, and during daytime hours; number of apnea and arousal events per occurrence of sleep; and amount of time spent in the various sleep states, e.g., the S3 and S4 sleep states. IMD 14 may store the determined values as sleep quality metric values 66 within memory 48.

Figure 6:
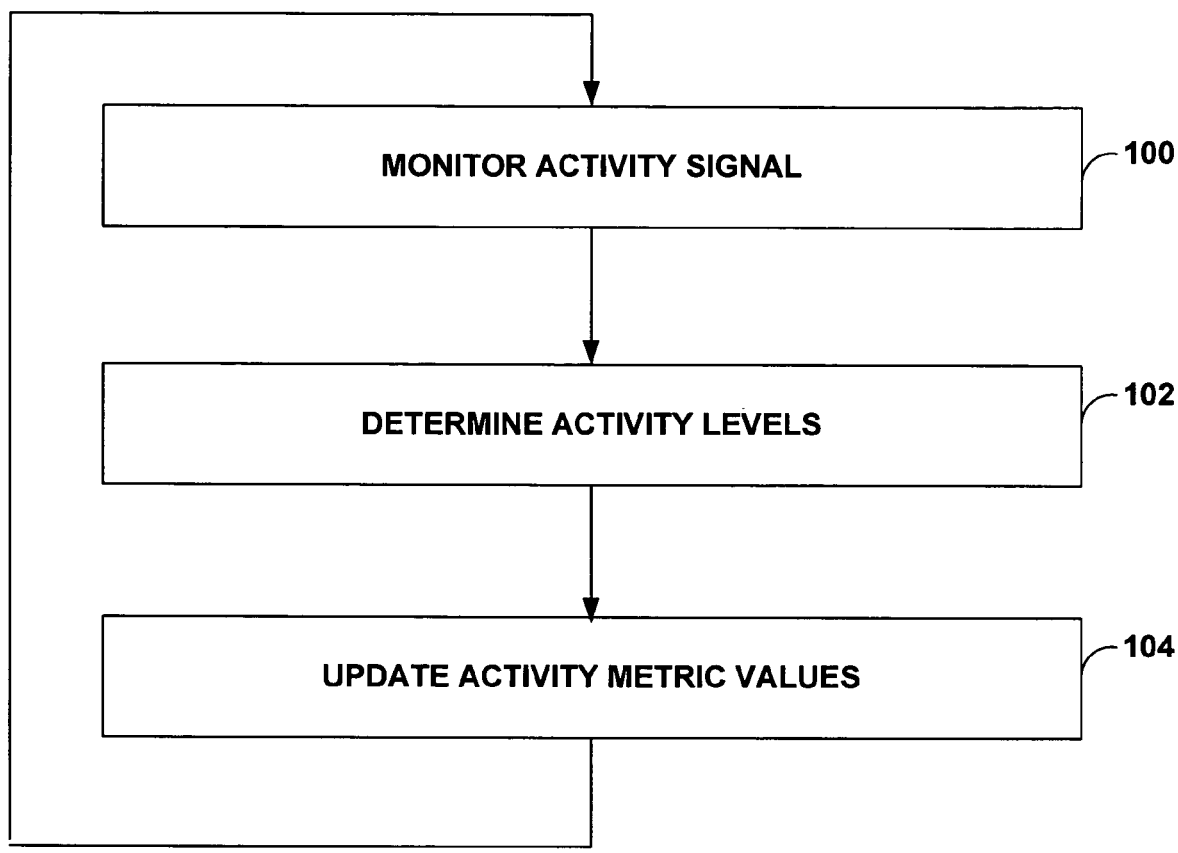
FIG. 6 is a flow diagram illustrating an example method for collecting activity information that may be employed by an implantable medical device.

FIG. 6 is a flow diagram illustrating an example method for collecting activity information that may be employed by IMD 14. IMD 14 monitors one or more signals that reflect patient activity generated by sensors 40 (100). For example, IMD 14 may monitor a signal generated by an accelerometer or piezoelectric crystal, and/or a signal that indicates a physiological parameter that varies as a function of patient activity, such as heart rate, respiration rate, respiratory volume, or muscle activity.

IMD 14 determines an activity level 62 (102) based on the one or more signals. For example, IMD 14 may determine a number of activity counts based on the one or more signals, as described above. IMD 14 may then update one or more activity metric values 66 based on the determined activity level (104).

IMD 14 may periodically perform the method illustrated in FIG. 6, i.e., periodically determine activity levels 62. IMD 14 need not update activity metric values 66 each time an activity level 62 is determined. In some embodiments, for example, IMD 14 may store activity levels 62 within memory, and may determine the activity metric values 66 upon receiving a request for the values from clinician programmer 20.

Figure 7:
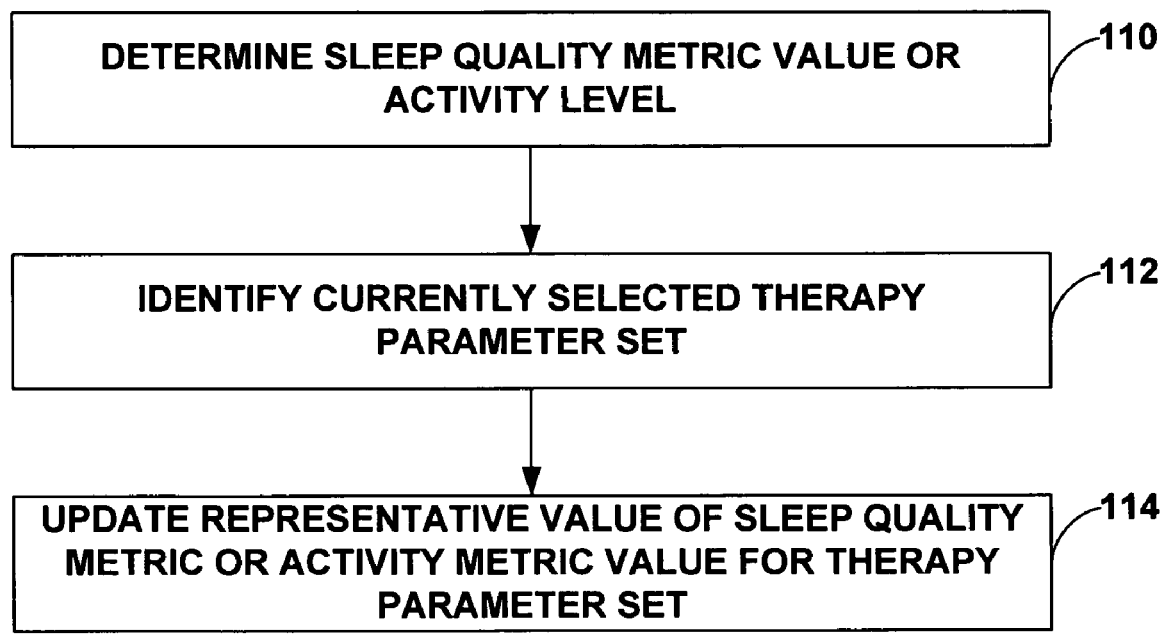
FIG. 7 is a flow diagram illustrating an example method for associating sleep quality information and activity information with therapy parameter sets that may be employed by an implantable medical device.

FIG. 7 is a flow diagram illustrating an example method for associating sleep quality information and activity information with therapy parameter sets that may be employed by IMD 14. IMD 14 determines a value 66 of a sleep quality metric or an activity level 62 according to any of the techniques described above (110). IMD 14 also identifies the current therapy parameter set 60, e.g., the therapy parameter set 60 used by IMD 14 to control delivery of therapy when patient 12 was asleep or when the activity level was determined (112), and associates the newly determined level or value with the current therapy parameter set 60.

Among sleep quality metric values 66 within memory 48, IMD 14 stores a representative value of the sleep quality metric, e.g., a mean or median value, for each of the plurality of therapy parameter sets 60. When IMD 14 determines a new sleep quality metric value, IMD 14 updates the representative values for the current therapy parameter set based on the newly determined sleep quality metric value (114). For example, a newly determined sleep efficiency value may be used to determine a new average sleep efficiency value for the current therapy parameter set 60. Similarly, among the activity metric values 68 within memory 48, IMD 14 stores an associated activity metric value. When IMD 14 determines a new activity level 62, IMD 14 updates the activity metric value 68 the current therapy parameter set based on the newly determined activity level.

Figure 8:
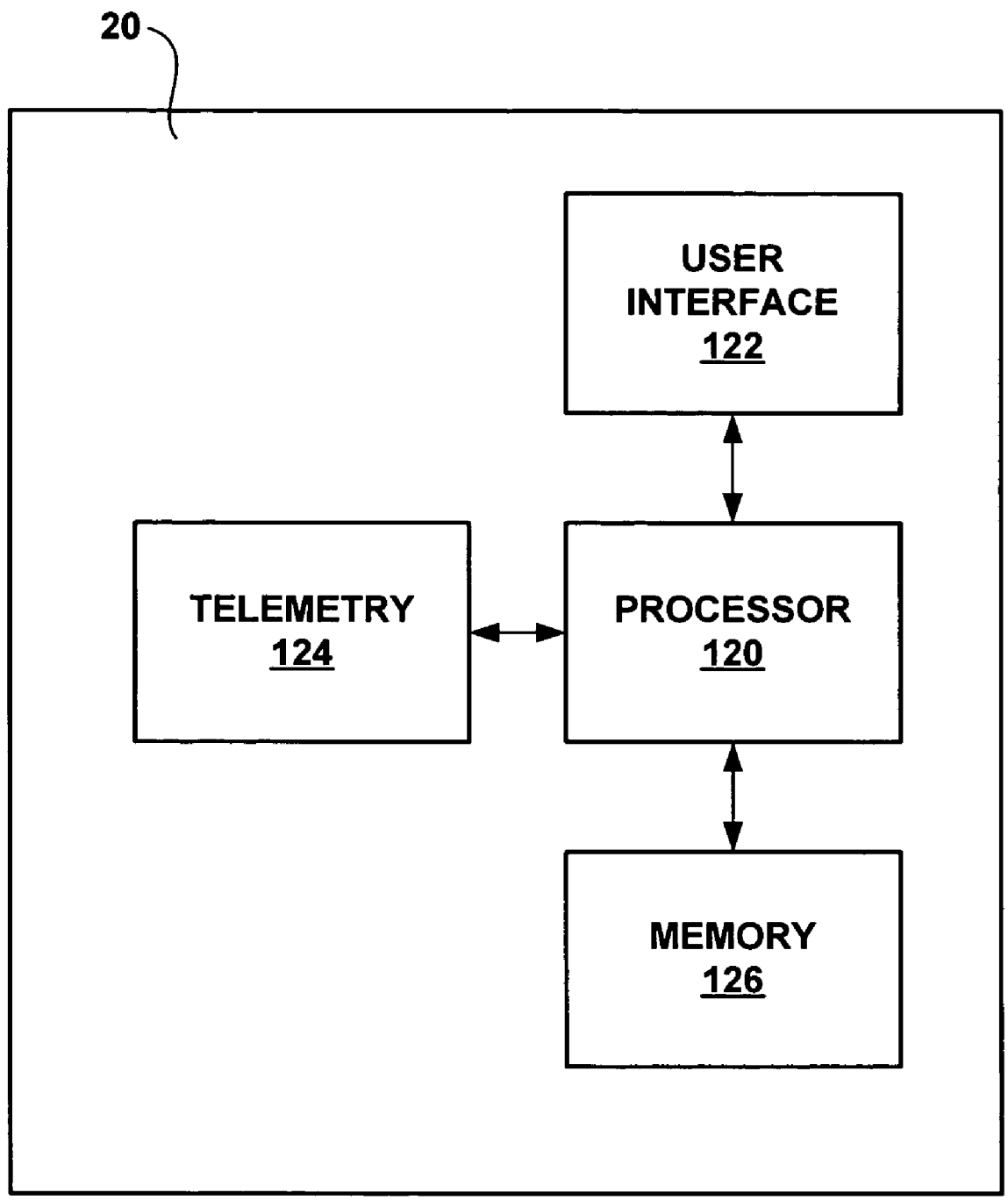
FIG. 8 is a block diagram illustrating an example clinician programmer.

FIG. 8 is a block diagram further illustrating clinician programmer 20. A clinician may interact with a processor 120 via a user interface 122 in order to program therapy for patient 12, e.g., specify therapy parameter sets. Processor 120 may provide the specified therapy parameter sets to IMD 14 via telemetry circuit 124.

At another time, e.g., during a follow up visit, processor 120 may receive activity levels 62, sleep quality metric values 66, and/or activity metric values 68 from IMD 14 via a telemetry circuit 124, and may generate sleep quality information or activity information for presentation to the clinician via user interface 122. For example, processor 120 may present a trend diagram of activity levels 62 or sleep quality metric values 66 over time, or a histogram, pie chart, or other illustration of percentages of time that activity levels 62 or sleep quality metric values 66 were within certain ranges. Processor 120 may generate such charts or diagrams using activity levels 62 and sleep quality metric values 66 associated with a particular one of the therapy parameter sets 60, or all of the activity levels 62 and sleep quality metric values 66 recorded by IMD 14.

Processor 120 may also receive information identifying a plurality of therapy parameter sets 60, and representative sleep quality metric values 66 and activity metric values associated with the therapy parameter sets 60, from IMD 14 via telemetry circuit 124. The therapy parameter sets 60 may include the originally specified parameter sets, and parameter sets resulting from manipulation of one or more therapy parameters by patient 12 using patient programmer 26. After receiving this information, processor 120 generates a list of the therapy parameter sets 60 and associated sleep quality metric values 66 and activity metric values 68, and presents the list to the clinician via user interface 122.

User interface 112 may include display 22 and keypad 24, and may also include a touch screen or peripheral pointing devices as described above. Processor 110 may include a microprocessor, a controller, a DSP, an ASIC, an FPGA, discrete logic circuitry, or the like. Clinician programmer 20 also includes a memory 116. Memory 116 may include program instructions that, when executed by processor 110, cause clinician programmer 20 to perform the functions ascribed to clinician programmer 20 herein. Memory 116 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

FIG. 9 illustrates an example list 130 of therapy parameter sets 60, associated sleep quality metric values 66, and associated activity metric values 68 that may be presented to a clinician by clinician programmer 20. Each row of example list 130 includes an identification of one of therapy parameter sets 60, the parameters of the set, a representative value for one or more sleep quality metrics associated with the identified therapy parameter set, and an associated value of at least one activity metric.

List 130 may include values for any number of sleep quality metrics and activity metrics. The illustrated example list 130 includes sleep efficiency, sleep latency and a percentage of time active. IMD 14 may determine the percentage of time active for one of parameter sets 60 by, for example, comparing each activity level 62 associated with the parameter set to an "active" threshold, i.e., a threshold indicative of significant physical activity, and determining the percentage of activity levels 62 above the threshold. As illustrated in FIG. 9, IMD 14 may also compare each activity level for the therapy parameter set to an additional, "high activity" threshold, and determine a percentage of activity levels 62 above that threshold.

Figure 10:
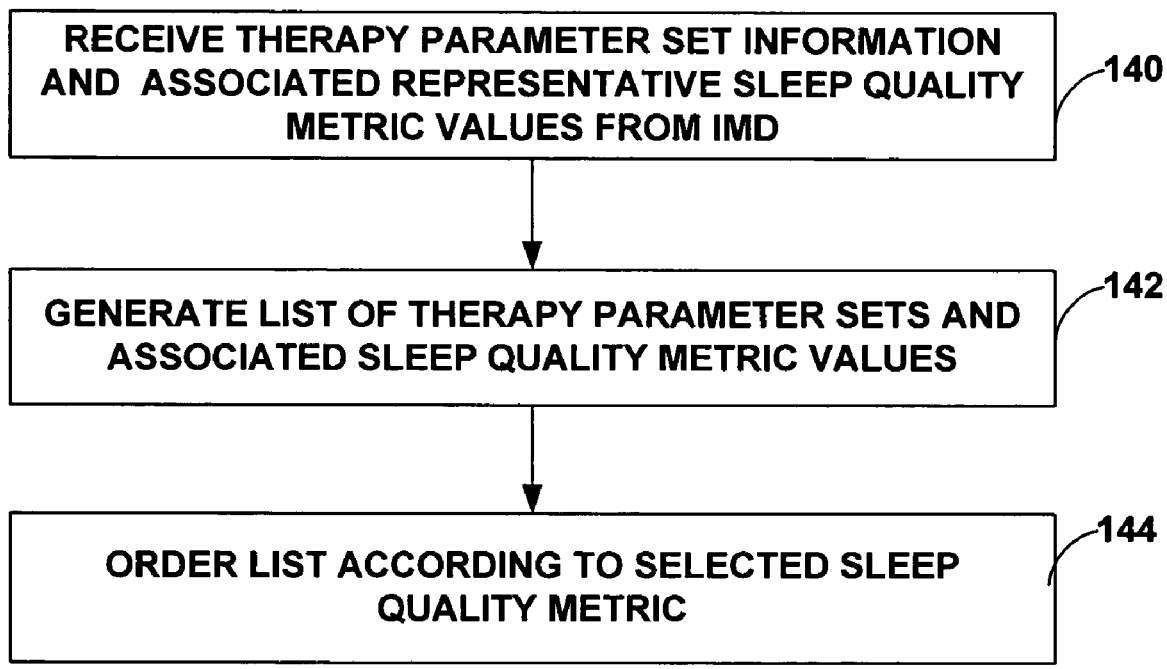
FIG. 10 is a flow diagram illustrating an example method for displaying a list of therapy parameter sets and associated sleep quality information and activity information that may be employed by a clinician programmer.

FIG. 10 is a flow diagram illustrating an example method for displaying a list 130 of therapy parameter sets and associated sleep quality and activity information that may be employed by clinician programmer 20. According to the example method, clinician programmer 20 receives information identifying the plurality of therapy parameter sets 60 stored in memory 48 of IMD 14, one or more representative sleep quality metric values associated with each of the therapy parameter sets, and one or more activity metric values associated with each of the activity sets (140). Clinician programmer 20 generates a list 130 of the therapy parameter sets 60, any associated representative sleep quality metric values, and any associated activity metric values (142), and orders the list according to a selected one of the sleep quality metrics or activity metrics (144). For example, in the example list 130 illustrated in FIG. 9, the clinician may select whether list 130 should be ordered according to sleep efficiency, sleep latency, or percentage of time active via user interface 122 of clinician programmer 20.

Various embodiments of the invention have been described. However, one skilled in the art will recognize that various modifications may be made to the described embodiments without departing from the scope of the invention. For example, a patient programming device, such as patient programmer 26, may additionally or alternatively receives sleep quality metric values and/or activity metric values from IMD 14, and may provide sleep quality or activity information to a user based on the sleep quality or activity metric values. Further details regarding provision of sleep quality information to a patient via a patient programming device may be found in a commonly-assigned and copending U.S. patent application Ser. No. 11/691,376 by Ken Heruth and Keith Miesel, entitled "COLLECTING SLEEP QUALITY INFORMATION VIA A MEDICAL DEVICE," filed on Apr. 15, 2004, which is incorporated herein by reference in its entirety.

As another example, although described herein primarily in the context of treatment of pain with an implantable neurostimulator, the invention is not so limited. The invention may be embodied in any implantable medical device, such as a cardiac pacemaker, an implantable pump, or an implantable monitor that does not itself deliver a therapy to the patient. Further, the invention may be implemented via an external, e.g., non-implantable, medical device. In such embodiments, the external medical device itself may include a user interface and display to present sleep quality and activity information to a user, such as a clinician or patient, based on determined sleep quality metric values.

As another example, the invention may be embodied in a trial neurostimulator, which is coupled to percutaneous leads implanted within the patient to determine whether the patient is a candidate for neurostimulation, and to evaluate prospective neurostimulation therapy parameter sets. Similarly, the invention may be embodied in a trial drug pump, which is coupled to a percutaneous catheter implanted within the patient to determine whether the patient is a candidate for an implantable pump, and to evaluate prospective therapeutic agent delivery parameter sets. Sleep quality metric values and activity metric values collected by the trial neurostimulator or pump may be used by a clinician to evaluate the prospective therapy parameter sets, and select parameter sets for use by the later implanted non-trial neurostimulator or pump. In particular, a trial neurostimulator or pump may determine representative values of one or more sleep quality metrics and activity metric values for each of a plurality of prospective therapy parameter sets, and a clinician programmer may present a list of prospective parameter sets and associated representative values to a clinician. The clinician may use the list to identify potentially efficacious parameter sets, and may program a permanent implantable neurostimulator or pump for the patient with the identified parameter sets.

In some embodiments, the implantable or external medical device does not determine whether the patient is attempting to sleep, determine values for sleep quality metrics, determine activity metric values, and/or periodically determine activity levels. Instead, in some embodiments, a computing device, such as one of programming devices 20, 26 performs one or more of these functions. For example, a programming device, and more particularly a processor of the programming device, e.g., processor 120, may receive physiological parameter values, activity levels, and/or samples of an activity signal from a medical device, and determine activity metric values and sleep quality metric values based on the information received from the medical device using any of the techniques described herein with reference to a medical device.

In some embodiments, the medical device may associate recorded physiological parameter values, signal samples, and/or activity levels with a current therapy parameter set, and may provide information identifying and plurality of therapy parameter sets and collected information associated with the therapy parameter sets to the programming device. In such embodiments, the programming device may determine representative sleep quality metric values and activity metric values associated with the various therapy parameter sets using any of techniques described herein with reference to a medical device. The programming device may receive such information from the medical device in real time, or may interrogate the medical device for information recorded by the medical device over a period of time.

The invention may also be embodied as a computer-readable medium that includes instructions to cause a processor to perform any of the methods described herein. These and other embodiments are within the scope of the following claims.

The invention claimed is:

1. A method comprising:
monitoring a plurality of physiological parameters of a patient via a medical device, wherein the plurality of physiological parameters includes at least one parameter indicative of patient physical activity monitored via at least one accelerometer;
determining when the patient is attempting to sleep;
determining when the patient is asleep based on at least one of the physiological parameters;
determining values of at least one sleep quality metric that is indicative of sleep quality based on at least one of when the patient is attempting to sleep, when the patient is asleep, or values of at least one of the physiological parameters when the patient is asleep;
periodically determining an activity level of the patient based on the at least one of the physiological parameters indicative of patient physical activity that is monitored via the at least one accelerometer; and
determining a value of at least one activity metric based on activity levels determined when the patient is not attempting to sleep.

2. The method of claim 1, wherein determining when the patient is attempting to sleep comprises receiving an indication from the patient that the patient is attempting to sleep.

3. The method of claim 1, wherein monitoring a plurality of physiological parameters comprises monitoring at least one signal that indicates posture of the patient, and determining when the patient is attempting to sleep comprises determining when the patient is recumbent.

4. The method of claim 3,
wherein the at least one accelerometer comprises a plurality of orthogonally aligned accelerometers, and
wherein monitoring at least one signal comprises monitoring a signal from each of the plurality of orthogonally aligned accelerometers, and determining when the patient is recumbent comprises determining when the patient is recumbent based on a DC component of each of the signals.

5. The method of claim 1, wherein determining when the patient is attempting to sleep comprises determining when the patient is attempting to sleep based on the activity levels of the patient.

6. The method of claim 5, wherein determining when the patient is attempting to sleep based on the activity levels comprises:
comparing the activity levels to an activity level threshold; and
comparing an amount of time that the activity levels remains substantially below the activity level threshold to a time threshold.

7. The method of claim 1, wherein monitoring a plurality of physiological parameters comprising monitoring a level of melatonin within a bodily fluid, and determining when the patient is attempting to sleep comprises determining when the patient is attempting to sleep based on the melatonin level.

8. The method of claim 1, wherein monitoring a plurality of physiological parameters comprises monitoring at least one of posture, heart rate, respiration rate, respiratory volume, or core temperature.

9. The method of claim 1, wherein monitoring a plurality of physiological parameters comprises monitoring at least one of blood pressure, blood oxygen saturation, partial pressure of oxygen within blood, partial pressure of oxygen within cerebrospinal fluid, muscular activity, arterial blood flow, or galvanic skin response.

10. The method of claim 1, wherein the sleep quality metric comprises sleep efficiency, and determining values of the sleep quality metric comprises
determining a percentage of time that the patient is asleep while the patient is attempting to sleep.

11. The method of claim 1, wherein the sleep quality metric comprises sleep latency, and determining values of the sleep quality metric comprises:
identifying a first time when the patient is attempting to fall asleep;
identifying a second time when the patient falls asleep; and
determining an amount of time between the first and second times.

12. The method of claim 1, wherein determining values of the sleep quality metric comprises
determining an amount of time that the patient is asleep during a period.

13. The method of claim 1, wherein determining values of the sleep quality metric comprises
identifying at least one of a number of arousal events and a number of apnea events during a period of sleep.

14. The method of claim 1, wherein determining values of the sleep quality metric comprises:
identifying when the patient is within a sleep state based on at least one of the physiological parameters; and
determining an amount of time that the patient was within the sleep state.

15. The method of claim 14, wherein the sleep state comprises at least one of an S3 sleep state and an S4 sleep state.

16. The method of claim 1, wherein determining a value of an activity metric comprises determining at least one of a mean and a median of determined activity levels.

17. The method of claim 16, wherein determining a value of an activity metric comprises:
comparing the at least one of the mean and the median activity level to at least one threshold; and
selecting the activity metric value from a plurality of predetermined possible activity metric values based on the comparison.

18. The method of claim 1, wherein determining a value of an activity metric comprises:
comparing each of the activity levels to a threshold value; and
determining at least one of a percentage of time above the threshold and a percentage of time below the threshold.

19. The method of claim 1, wherein determining a value of an activity metric comprises:
comparing each of the activity levels to a threshold value; and
determining an average length of time that consecutively determined activity levels were above the threshold.

20. The method of claim 1, wherein periodically determining an activity level comprises periodically determining a number of activity counts.

21. The method of claim 1, wherein the medical device delivers a therapy to the patient according to a plurality of therapy parameter sets, the method further comprising:
associating each of the determined sleep quality metric values and each of the determined activity levels with one or more of the plurality of therapy parameter sets that was used by the medical device to deliver therapy when that value or level was determined;
for each of the plurality of therapy parameter sets, determining a representative value of each of the at least one sleep quality metric based on the sleep quality metric values associated with the therapy parameter set; and
for each of the plurality of therapy parameter sets, determining at least one activity metric value based on the activity levels associated with the therapy parameter set.

22. The method of claim 21, further comprising presenting a list of the therapy parameter sets, associated representative sleep quality metric values, and associated activity metric values.

23. The method of claim 22, further comprising ordering the list of therapy parameter sets according to values of a user selected one of the sleep quality metrics and activity metrics.

24. The method of claim 1, wherein the medical device comprises an implantable medical device.

25. The method of claim 24, wherein the implantable medical device comprises at least one of an implantable neurostimulator and an implantable drug pump.

26. The method of claim 1, wherein the medical device comprises at least one of a trial neurostimulator and a trial pump.

27. The method of claim 1, further comprising indicating efficacy of a pain therapy based on the values of the at least one sleep quality metric and the value of the at least one activity metric.

28. The method of claim 1, further comprising indicating efficacy of spinal cord stimulation based on the values of the at least one sleep quality metric and the value of the at least one activity metric.

* * * * *